United States Patent
Coe et al.

(10) Patent No.: US 8,764,735 B2
(45) Date of Patent: Jul. 1, 2014

(54) DETACHABLE END EFFECTORS

(71) Applicant: Ethicon Endo-Surgery, Inc., Cincinnati, OH (US)

(72) Inventors: Jonathan A. Coe, Boulder, CO (US); James W. Voegele, Cincinnati, OH (US); Gary L. Long, Cincinnati, OH (US); Andrew M. Zwolinski, Cincinnati, OH (US); Kyle P. Moore, Mason, OH (US); Robert P. Gill, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 13/742,040

(22) Filed: Jan. 15, 2013

(65) Prior Publication Data
US 2013/0138091 A1    May 30, 2013

Related U.S. Application Data

(63) Continuation of application No. 11/693,976, filed on Mar. 30, 2007, now Pat. No. 8,377,044.

(51) Int. Cl.
*A61B 17/00* (2006.01)
(52) U.S. Cl.
USPC ........ 606/1; 606/41; 606/45; 606/47; 606/49; 606/50
(58) Field of Classification Search
USPC ...................................... 606/1–52
See application file for complete search history.

(56) References Cited

U.S. PATENT DOCUMENTS

| | | | |
|---|---|---|---|
| 5,201,743 | A | 4/1993 | Haber et al. |
| 5,282,806 | A | 2/1994 | Haber et al. |
| 5,286,255 | A | 2/1994 | Weber |
| 5,308,357 | A | 5/1994 | Lichtman |
| 5,330,502 | A | 7/1994 | Hassler et al. |
| 5,352,219 | A | 10/1994 | Reddy |
| 5,417,203 | A | 5/1995 | Tovey et al. |
| 5,441,059 | A | 8/1995 | Dannan |
| 5,468,250 | A | 11/1995 | Paraschac et al. |
| 5,502,698 | A | 3/1996 | Mochizuki |

(Continued)

FOREIGN PATENT DOCUMENTS

| | | |
|---|---|---|
| DE | 10 14 9421 A1 | 4/2003 |
| EP | 1 709 900 A1 | 10/2006 |

(Continued)

*Primary Examiner* — Aaron Roane
(74) *Attorney, Agent, or Firm* — Mintz Levin Colin Ferris Glovsky and Popeo, P.C.

(57) ABSTRACT

Methods and devices are provided for performing various procedures using interchangeable end effectors. In general, the methods and devices allow a surgeon to remotely and selectively attach various interchangeable surgical end effectors to a shaft located within a patient's body, thus allowing the surgeon to perform various procedures without the need to remove the shaft from the patient's body. In an exemplary embodiment, multiple end effectors can be introduced into a body cavity. The end effectors can be disassociated or separate from one another such that they float within the body cavity. A distal end of a shaft can be positioned within the body cavity and it can be used to selectively engage one of the end effectors. In particular, the device can be configured to allow each end effector to be remotely attached and detached from the distal end of the shaft.

20 Claims, 22 Drawing Sheets

(56) References Cited

U.S. PATENT DOCUMENTS

| | | |
|---|---|---|
| 5,578,052 A | 11/1996 | Koros et al. |
| 5,593,402 A | 1/1997 | Patrick |
| 5,613,937 A | 3/1997 | Garrison et al. |
| 5,618,303 A | 4/1997 | Marlow et al. |
| 5,716,326 A | 2/1998 | Dannan |
| 5,810,877 A | 9/1998 | Roth et al. |
| 5,928,263 A | 7/1999 | Hoogeboom |
| 5,980,455 A | 11/1999 | Daniel et al. |
| 6,024,748 A | 2/2000 | Manzo et al. |
| 6,059,719 A | 5/2000 | Yamamoto et al. |
| 6,159,200 A | 12/2000 | Verdura et al. |
| 6,309,397 B1 | 10/2001 | Julian et al. |
| 6,419,688 B1 | 7/2002 | Bacher et al. |
| 6,595,984 B1 | 7/2003 | DeGuillebon |
| 6,626,824 B2 | 9/2003 | Ruegg et al. |
| 6,635,071 B2 | 10/2003 | Boche et al. |
| 6,770,081 B1 | 8/2004 | Cooper et al. |
| 6,827,712 B2 | 12/2004 | Tovey et al. |
| 6,860,878 B2 | 3/2005 | Brock |
| 6,869,395 B2 | 3/2005 | Page et al. |
| 6,884,213 B2 | 4/2005 | Raz et al. |
| 7,122,028 B2 | 10/2006 | Looper et al. |
| 7,125,403 B2 | 10/2006 | Julian et al. |
| 7,241,290 B2 | 7/2007 | Doyle et al. |
| 7,297,142 B2 | 11/2007 | Brock |
| 7,331,967 B2 | 2/2008 | Lee et al. |
| 7,559,887 B2 | 7/2009 | Dannan |
| 7,604,642 B2 | 10/2009 | Brock |
| 7,699,835 B2 | 4/2010 | Lee et al. |
| 7,862,553 B2 | 1/2011 | Ewaschuk |
| 8,057,502 B2 | 11/2011 | Maliglowka et al. |
| 8,377,044 B2 | 2/2013 | Coe et al. |
| 2004/0152941 A1 | 8/2004 | Asmus et al. |
| 2005/0131396 A1 | 6/2005 | Stanczak et al. |
| 2005/0215983 A1 | 9/2005 | Brock |
| 2005/0250984 A1 | 11/2005 | Lam et al. |
| 2006/0079933 A1 | 4/2006 | Hushka et al. |
| 2006/0184161 A1 | 8/2006 | Maahs et al. |
| 2006/0190035 A1 | 8/2006 | Hushka et al. |
| 2007/0093792 A1 | 4/2007 | Julian et al. |
| 2008/0015413 A1 | 1/2008 | Barlow et al. |
| 2008/0015552 A1 | 1/2008 | Doyle et al. |
| 2008/0045003 A1 | 2/2008 | Lee et al. |
| 2008/0140090 A1 | 6/2008 | Aranyi et al. |
| 2008/0142005 A1 * | 6/2008 | Schnell .................. 128/200.26 |
| 2008/0154299 A1 | 6/2008 | Livneh |
| 2008/0242939 A1 | 10/2008 | Johnston |
| 2008/0243106 A1 | 10/2008 | Coe et al. |
| 2008/0287926 A1 | 11/2008 | Abou El Kheir |
| 2009/0005636 A1 | 1/2009 | Pang et al. |
| 2009/0005638 A1 | 1/2009 | Zwolinski |
| 2011/0208007 A1 | 8/2011 | Shohat et al. |
| 2012/0316575 A1 | 12/2012 | Farin et al. |

FOREIGN PATENT DOCUMENTS

| | | |
|---|---|---|
| JP | 2005/261734 A | 9/2005 |
| WO | 2008/015666 A2 | 2/2008 |
| WO | 2011/089565 A1 | 7/2011 |
| WO | 2012/035524 A2 | 3/2012 |
| WO | 2012/126967 A2 | 9/2012 |
| WO | 2013/007764 A1 | 1/2013 |

* cited by examiner

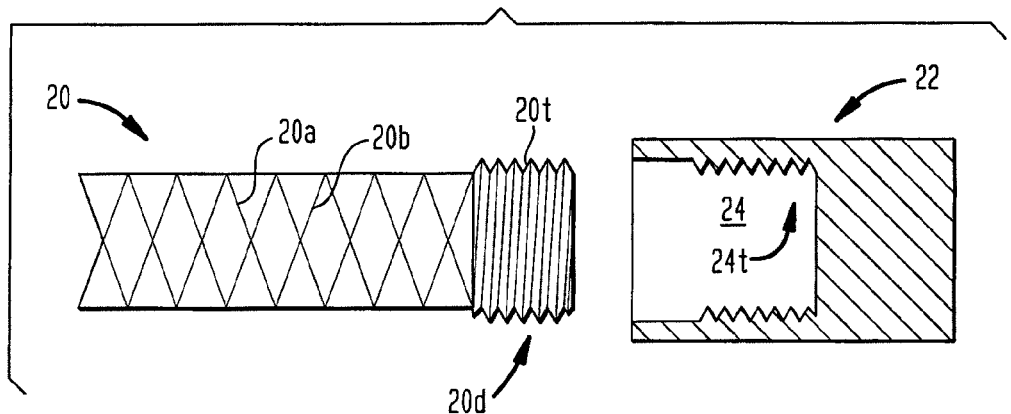
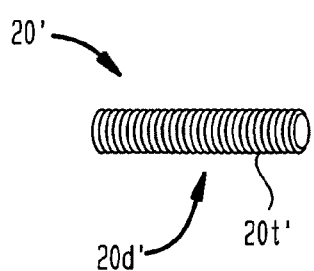
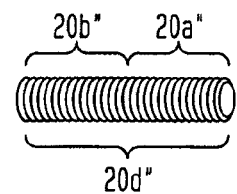
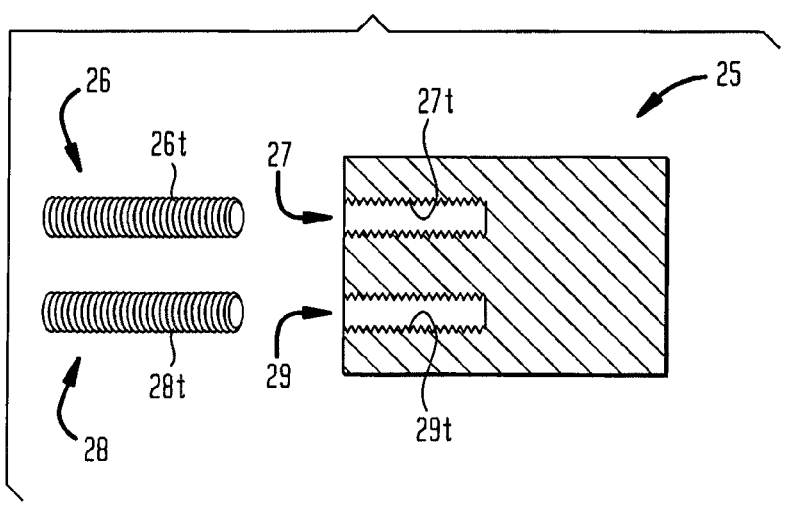

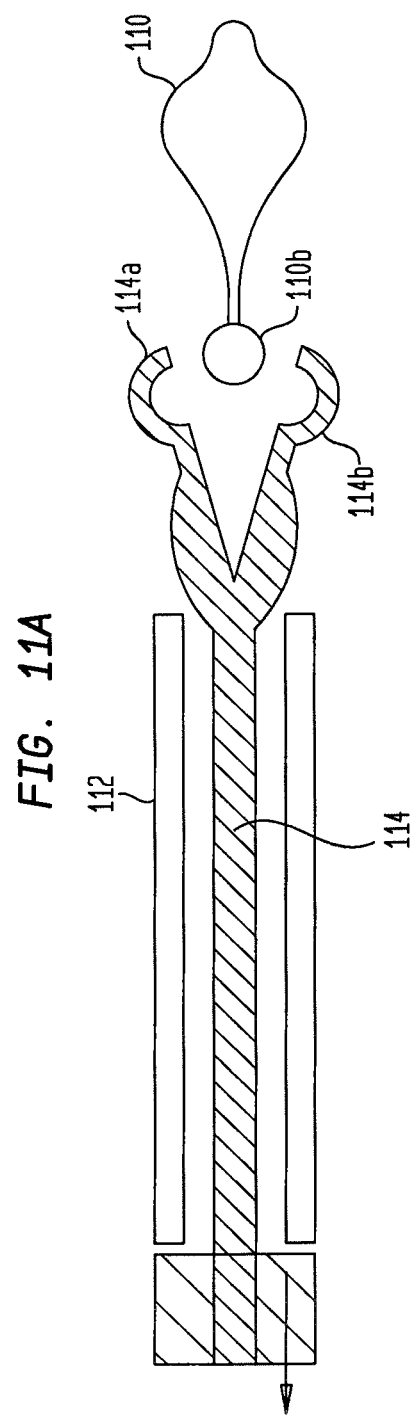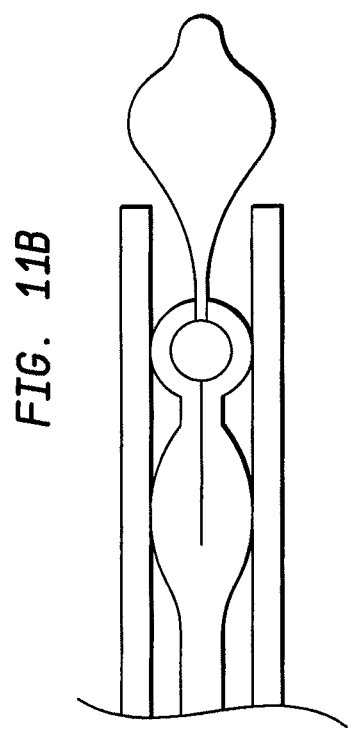
FIG. 11A
FIG. 11B

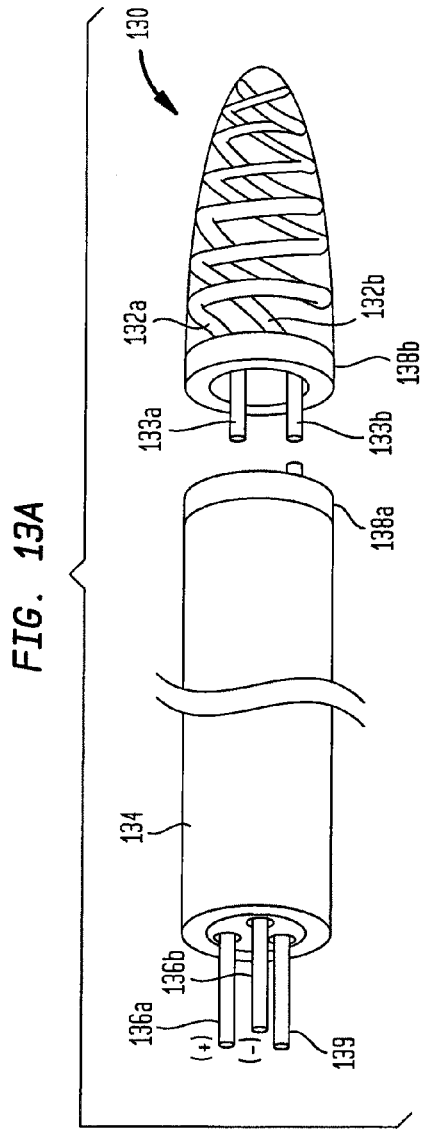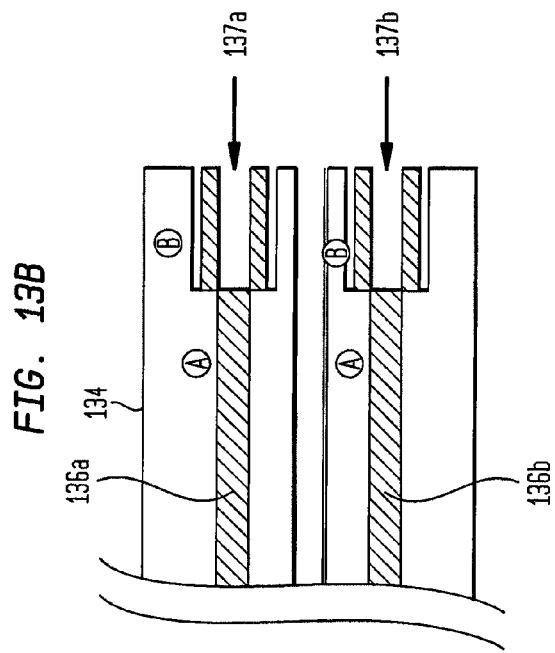
FIG. 13A
FIG. 13B

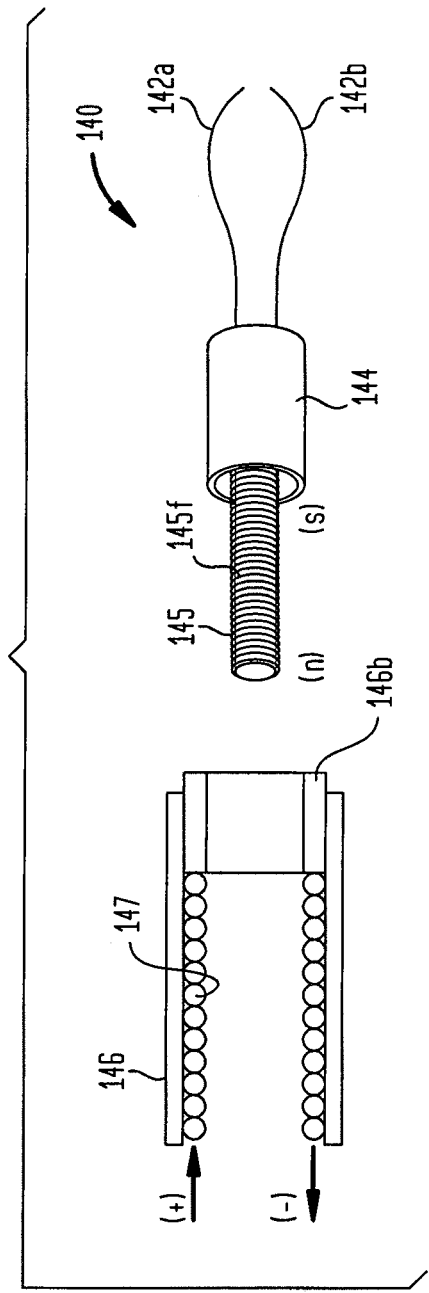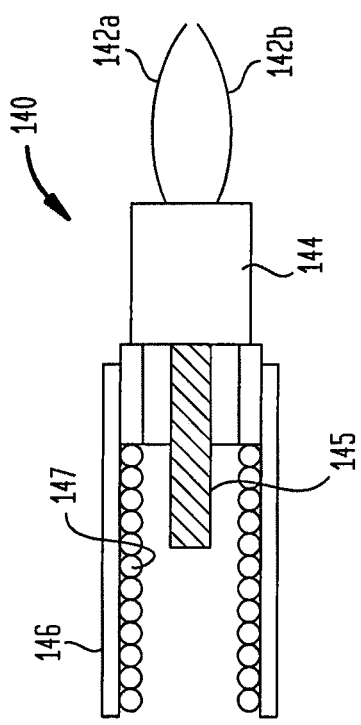
FIG. 14A
FIG. 14B

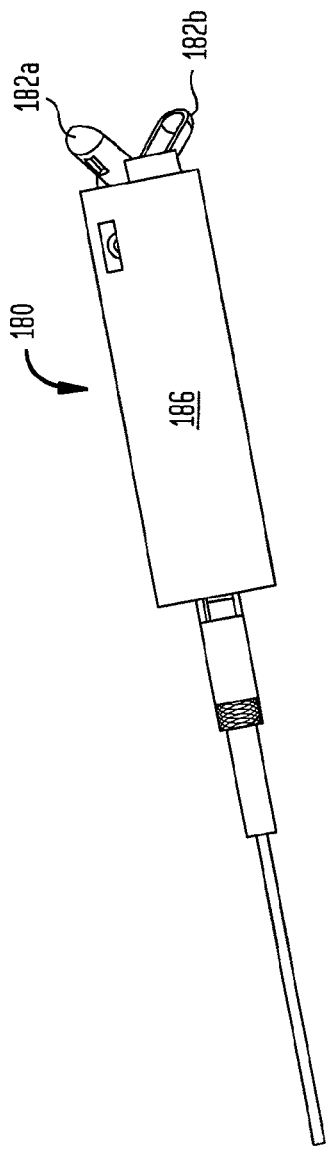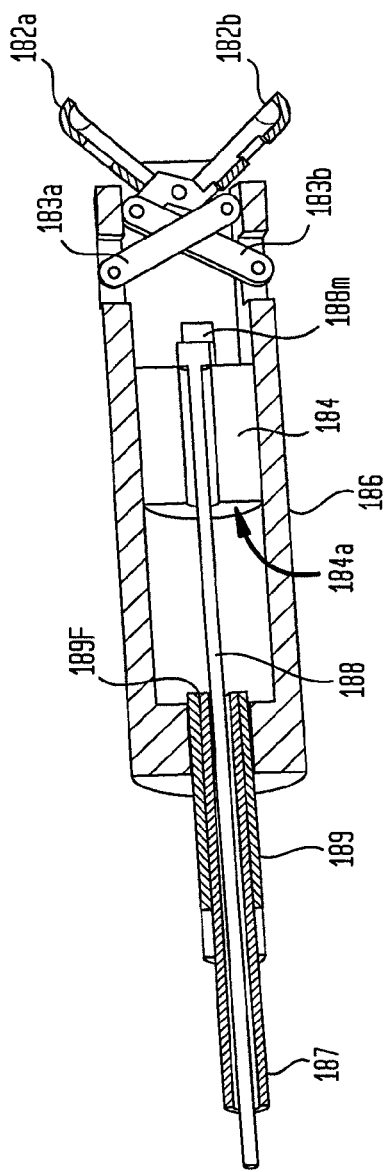
FIG. 18A
FIG. 18B

DETACHABLE END EFFECTORS

CROSS REFERENCE TO RELATED APPLICATIONS

This application is a continuation of U.S. patent application Ser. No. 11/693,976 filed on Mar. 30, 2007 and entitled "Detachable End Effectors," which is hereby incorporated by reference in its entirety.

FIELD OF THE INVENTION

The present invention relates to methods and devices for performing surgical procedures using interchangeable end effectors.

BACKGROUND OF THE INVENTION

As the range of therapeutic endolumenal and transgastric treatments available to gastroenterologists and surgeons expands, the tools used to perform such procedures are becoming more complex. Increasingly sophisticated maneuvers demand greater functionality within the limited space offered by the gastrointestinal tract. Consequently, the size of surgical end effectors developed to achieve this functionality will increase, preventing operation through a working channel of an endoscope, which is the traditional approach to endoscopic procedures. Unfortunately, if an instrument is not passed through an endoscope, articulation and control of a distal end of the instrument is difficult if not impossible.

Instruments have been developed that do provide control of tools extending tangential to an endoscope. For example, accessory channels that run along side an endoscope have been developed with steering mechanisms at the distal end for effecting movement of a tool inserted therethrough. While this provides the advantage of articulation independent of a working channel, the size of the tool cannot exceed the diameter of the body lumen, e.g., the esophagus, less the diameter of the endoscope.

Accordingly, there remains a need for methods and devices for delivering end effectors through a body lumen without the size constraints required by a working channel, yet that allows for endoscopic control. There also remains a need for methods and devices for performing multiple surgical procedures using multiple end effectors without the need to exchange the end effectors through the working channel of an endoscope.

SUMMARY OF THE INVENTION

The present invention generally provides methods and devices for performing various procedures using interchangeable end effectors. In general, the methods and devices allow a surgeon to remotely and selectively attach various interchangeable surgical end effectors to a shaft located within a patient's body, thus allowing the surgeon to perform various procedures without the need to remove the shaft from the patient's body. In one embodiment, a modular surgical device is provided and includes a shaft having proximal and distal ends, a plurality of end effectors interchangeably matable to the distal end of the shaft, and an engagement mechanism located on the distal end of the shaft and configurable between a first position in which the engagement mechanism mates one of the plurality of end effectors to the distal end of the shaft, and a second position in which the plurality of end effectors are disassociated from the shaft and from one another. The engagement mechanism can be configured for mating the end effectors and the shaft in situ without assistance from additional devices. The device can also include a second shaft extending adjacent to the first shaft and having a second engagement mechanism formed thereon and adapted to mate one of the plurality of end effectors to the second shaft such that movement of the second shaft is effective to actuate the end effector.

The engagement mechanism can have a variety of configurations. In one embodiment, the engagement mechanism can be threads formed on a distal end of the shaft and adapted to mate with corresponding threads formed in a bore in at least one of the plurality of end effectors. The device can also include an anti-rotation mechanism formed on at least one of an outer sleeve disposed over the shaft and the plurality of end effectors. The anti-rotation mechanism can be adapted to maintain at least one of the plurality of end effectors in a fixed position relative to the outer sleeve. In one embodiment, the anti-rotation mechanism can be an asymmetrical bore formed in one of the outer sleeve and at least one of the plurality of end effectors, and a protrusion formed on the other one of the outer sleeve and at least one of the plurality of end effectors. The protrusion can be adapted to be received within the bore to prevent rotation. In another embodiment, the anti-rotation mechanism can be first and second magnets formed on the outer sleeve and the end effector for magnetic engagement. In yet another embodiment, the anti-rotation mechanism can be a grasping element formed on the outer sleeve and adapted to grasp at least one of the plurality of end effectors.

In yet another embodiment, the engagement mechanism can be a magnet formed on the distal end of the shaft and adapted to magnetically engage a magnet formed on at least one of the plurality of end effectors. The engagement mechanism can also include a pusher disposed through the shaft and adapted to push an end effector out of engagement with the shaft. In an exemplary embodiment, the magnet on the shaft and the magnet on at least one of the plurality of end effectors are adapted to magnetically align with one another in a predetermined orientation.

In other embodiments, the engagement mechanism can be a male member adapted to mate with a female member formed on at least one of the plurality of end effectors. The male and female members can be, for example, a pin and bore, a hook and loop, and a ball and grasper. In another embodiment, the engagement mechanism can be a plurality of deflectable members formed on the shaft and adapted to be disposed within a bore formed in at least one of the plurality of end effectors. The device can also include an inner shaft disposed within the shaft and adapted to expand the deflectable members into engagement with the bore formed in at least one of the plurality of end effectors. In yet another embodiment, the engagement mechanism can be an electromagnetic coil disposed within a distal end of the shaft and adapted to engage a magnetic shaft formed on at least one of the plurality of end effectors.

Various end effectors can also be used with the device including, for example, a needle, a snare, a needle knife, a monopolar probe, a bipolar probe, a clipping device, a retractor, a band ligator, scissors, graspers, irrigation devices, marking devices, etc.

In another embodiment, a modular surgical device is provided and includes an elongate member having a proximal end with an actuator and a distal end with a mating element, and a plurality of end effectors for performing surgical procedures. Each end effector can include a mating element adapted to mate to the mating element on the elongate member such that the plurality of end effectors are interchangeably matable to the elongate member. In use, movement of the actuator is effective to cause the mating element on the distal end of the elongate member to interchangeably attach and detach the plurality of end effectors to the elongate member to allow the plurality of end effectors to be selectively and interchangeably mated to the elongate member when the end effectors are disposed within a body cavity. The mating element on the elongate member can have a variety of configurations, and it can be, for example, threads, a magnet, a grasping element, a piston, a pin, a hook, a deflectable member, and an electromagnetic element. The device can also include a second elongate member extending adjacent to the first elongate member and having a mating element adapted to mate to a corresponding mating element on at least one of the plurality of end effectors. Movement of a second actuator on the second elongate member can be effective to actuate the end effector.

In yet another embodiment, a surgical method is provided and includes delivering a plurality of end effectors to a body cavity of a patient, such as the stomach, such that the end effectors are disassociated within one another and float within the body cavity. A distal end of a shaft is positioned within the body cavity and a proximal end of the shaft extends from the patient. An actuator on the proximal end of the shaft can be manipulated to cause the distal end of the shaft to removably mate to one of the plurality of end effectors. Manipulating the actuator can be effective to cause an engagement mechanism located on the distal end of the shaft to engage and removably mate one of the plurality of end effectors to the distal end of the shaft. Manipulating the actuator can also be effective to detach the end effector from the distal end of the shaft. In one embodiment, the method can further include manipulating a second actuator on a second shaft to mate a distal end of the second shaft to the end effector that is mated to the first shaft. The second shaft can be moved relative to the first shaft to perform a surgical procedure with the end effector. In an exemplary embodiment the shaft is disposed through an endoscope.

BRIEF DESCRIPTION OF THE DRAWINGS

The invention will be more fully understood from the following detailed description taken in conjunction with the accompanying drawings, in which:

FIG. 2A is a side, partially cross-sectional view of one embodiment of an engagement mechanism that utilizes a threaded connection;

FIG. 2B is a side view of an alternate embodiment of a threaded shaft for use with the engagement mechanism of FIG. 2A;

FIG. 2C is a side view of another embodiment of a threaded shaft for use with the engagement mechanism of FIG. 2A;

FIG. 2D is a side, partially cross-sectional view of another embodiment of an engagement mechanism that utilizes two threaded connections;

FIG. 11A is a cross-sectional view of another embodiment of an end effector in the form of a snare that uses a ball and grasper engagement mechanism;

FIG. 11B is a cross-sectional view of the snare of FIG. 11A, showing the grasper engaging the ball on the snare to mate the snare to a shaft;

FIG. 13A is a side view of yet another embodiment of an end effector in the form of a bi-polar probe that uses a magnetic engagement mechanism with an alignment feature;

FIG. 13B is a cross-sectional view of a distal end of a shaft of FIG. 13A for mating to the probe;

FIG. 14A is a side partially cross-sectional view of an end effector in the form of a clipping device that uses an electromagnetic engagement mechanism according to yet another embodiment;

FIG. 14B is a side partially cross-sectional view of the clipping device of FIG. 14A showing the device mated to a shaft;

FIG. 18A is a side view of yet another embodiment of an end effector in the form of grasper;

FIG. 18B is a cross-sectional view of the scissors of FIG. 18A, showing expanding fingers mating the grasper to a shaft, and a male/female engagement mechanism for actuator the grasper;

DETAILED DESCRIPTION OF THE INVENTION

Figure 1A:
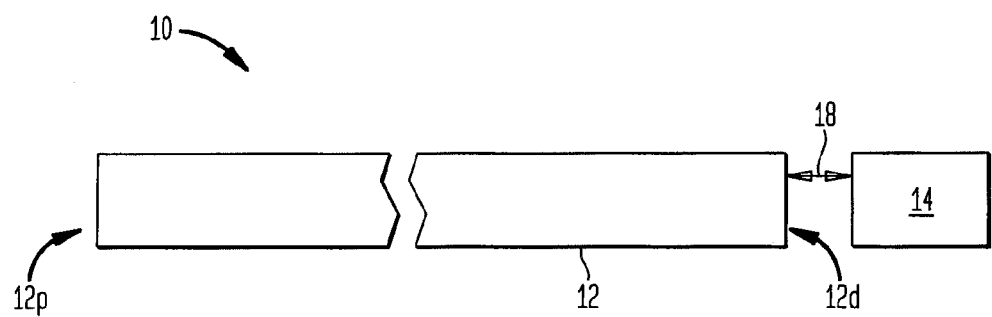
FIG. 1A is a schematic illustration of a generic modular device having interchangeable end effectors, showing one engagement mechanism.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for performing various procedures using interchangeable end effectors. In general, the methods and devices allow a surgeon to remotely and selectively attach various interchangeable surgical end effectors to a shaft located within a patient's body, thus allowing the surgeon to perform various procedures without the need to remove the shaft from the patient's body. Such a configuration also eliminates the size constraints of a working channel, as the end effectors do not need to be passed through a working channel since they are not attached to the shaft. Rather, the end effectors can be predisposed within the body cavity. In an exemplary embodiment, multiple end effectors can be introduced into a body cavity. The end effectors can be disassociated or separate from one another such that they float within the body cavity. A distal end of a shaft can be positioned within the body cavity and it can be used to selectively engage one of the end effectors. In particular, the device can be configured to allow each end effector to be remotely attached and detached from the distal end of the shaft. For example, a surgeon can actuate an actuation mechanism on the proximal end of the shaft to mate one of the end effectors to the distal end of the shaft without assistance from other tools and devices. After use of the end effector, the end effector can be released and another end effector can be remotely attached to the distal end of the shaft.

A person skilled in the art will appreciate that the devices disclosed herein can be used in numerous surgical procedures. By way of non-limiting example, the devices can be used in endoscopic procedures, in which the device is introduced into the body through a natural orifice, such as the oral, nasal, anal, or vaginal cavities. For example, the shaft of the device can be flexible and it can be advanced intraluminally, e.g., through the esophagus or colon, to position a distal end of the shaft at a surgical site. The surgical site can be located within the lumen or within a body cavity or organ accessed via the lumen. The devices can also be used in laparoscopic procedures, in which the device is introduced percutaneously. For example, the shaft can be rigid or flexible and it can be inserted through tissue to access a body cavity, such as the peritoneal cavity, or to access a hollow organ or a body lumen. The modular devices can also be used in procedures that include a combination of endoscopic and laparoscopic techniques.

A person skilled in the art will also appreciate that the particular configuration of the end effector can vary depending on the type of procedure being performed, and that the term "end effector" as used herein is intended to include any device that is configured to affect a particular surgical outcome. By way of non-limiting example, suitable end effectors include mono-polar coagulators and probes, bi-polar coagulators and probes, graspers, biopsy forceps, clipping devices, retractors, scissors, band ligators, suction devices, needles, needle knives and other cutting devices, sphinctertomes, snares, irrigation devices, marking devices, etc.

Figure 1B:
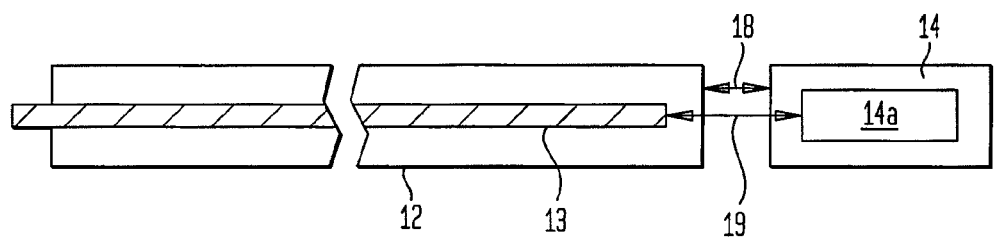
FIG. 1B is a schematic illustration of a generic modular device having interchangeable end effectors, showing two engagement mechanisms.

FIGS. 1A and 1B are schematic illustrations of a generic modular device 10 having interchangeable end effectors. In the embodiment shown in FIG. 1A, the device 10 generally includes an elongate member 12 having proximal and distal ends 12p, 12d. The particular configuration of the elongate member 12 can vary depending on the type of procedure being formed. For example, for endoscopic procedures the elongate member 12 can have a generally elongate flexible configuration, and the proximal end 12p can be configured to remain outside of a patient's body while the distal end 12d can be configured to be positioned within the patient's body. The elongate member 12 can also be solid or it can include one of more lumens formed therethrough. The cross-sectional shape of the elongate member 12 can also vary and does not need to be tubular. Portions, such as the distal end, can also have a tapered configuration or some other shape to facilitate mating to an end effector. The distal end can also include other features to facilitate mating, such as a water-tight seal, etc. The elongate member 12 can also be adapted to be disposed through an endoscope, or it can be integrally formed with an endoscope. FIG. 1A also illustrates a generic end effector 14 that is adapted to removably mate to the elongate member 12. The generic end effector 14 is intended to represent any end effector used to effect a particular surgical outcome. The device 10 further includes a first engagement mechanism, generically illustrated by arrow 18, that is coupled between the elongate member 12 and the end effector 14. Depending on the particular configuration of the end effector, the device 10 can also optionally include a second engagement mechanism, generically illustrated by arrow 19, that is coupled between a second elongate member 13 and a portion 14a of the end effector 14, as shown in FIG. 1B.

In use, each engagement mechanism 18, 19 can be configured to effect a particular action. For example, the first engagement mechanism 18 can be configured to perform the action of attaching and detaching the end effector 14 to and from the elongate member 12. The elongate member 12 can be used to selectively toggle the engagement mechanism 18 between a disengaged position in which the end effector 14 is disassociated from the distal end 12d of the elongate member 12 and can thus float within the body cavity, and an engaged position in which the end effector 14 is mated to the distal end 12d of the elongate member 12. This allows a surgeon to remotely attach and detach an end effector 14 to the distal end 12d of the elongate member 12, thus allowing multiple end effectors 14 to be interchangeably mated to the distal end 12d of the elongate member 12 without removing the device 10 from the patient's body and without assistance from other tools and devices. Where the device 10 includes a second engagement mechanism 19, as shown in FIG. 1B, the second engagement mechanism 19 can be configured to effect a second distinct action. The particular action is dependent on the configuration of the end effector 14. For example, where the end effector 14 is in the form of a clip applier having a pair of opposed jaws pivotally coupled to one another, the first engagement mechanism 18 can attach and detach the clip applier to and from the elongate member 12 of the device 10, and the second engagement mechanism 19 can couple to a portion 14a of the end effector 14, e.g., to the jaws of the clip applier, to effect the action of opening and closing the jaws. The second elongate member 13 can be used to actuate the second engagement mechanism 19. While not shown, the end effector can also be capable of performing a third action, such as advancing and firing a clip or staple from the jaws. Thus, a third engagement mechanism can be provided to effect the action of advancing and firing a clip or staple from the jaws. A third elongate member can be used to actuate the third engagement mechanism. Accordingly, the modular device can include any number of engagement mechanisms, and the particular quantity can be dependent on the particular quantity of actions that the end effector is capable of performing. Certain engagement mechanisms can also be configured to perform multiple actions. For example, a single engagement mechanism can be used to close the jaws of a clip applier and to fire a clip from the jaws.

FIGS. 2A-9 illustrate various exemplary engagement mechanisms that can be used to perform different actions, such as attachment/detachment, axial translation (also referred to as push/pull), and axial rotation. Each action can produce a desired outcome, such a clip firing, jaw opening/closing, etc. While particular engagement mechanisms are described and illustrated in connection with effecting particular actions, a person skilled in the art will appreciate that each engagement mechanism can be modified to perform any action. Moreover, the various engagement mechanisms can be used alone or in various combinations with one another.

FIGS. 2A-3E illustrate various exemplary engagement mechanisms that utilize a threaded connection to attach/detach an end effector to an elongate shaft, and/or to actuate the end effector. In the embodiment shown in FIG. 2A, a pure threaded connection is used to mate the end effector 22 and an elongate shaft 20. In particular, the elongate shaft 20 includes threads 20t formed around a distal end 20d thereof, and the end effector 22 includes a lumen 24 having threads 24t formed around an inner surface thereof. The distal end 20d of the elongate shaft 20 can be introduced into the lumen 24 and rotated relative to the end effector 22 to thereby threadably mate the shaft 20 to the end effector 22. A person skilled in the art will appreciate that the threaded connection can be reversed. That is, the threaded bore can be formed in the elongate shaft 20 and the end effector 22 can include a shaft with threads formed therearound.

FIG. 2A also illustrates one exemplary technique for enhancing the torsional stiffness of the elongate shaft 20 to facilitate attachment and detachment of an end effector 22 to and from the elongate shaft 20, to actuate a portion of the end effector 22, or to effect other motions and actions. This technique is particularly advantageous for use with endoscopic devices, in which the rotational motion is translated down a relatively long shaft that extends from outside of a patient's body through a body lumen. Given the long length and flexible construction of most flexible shafts, the shafts are often fairly compliant in torsion. Thus, it is advantageous to enhance the torsional strength of the shaft to facilitate the transfer of rotational motion from the proximal end of the shaft to the distal end of the shaft. As shown in FIG. 2A, this can be achieved using one or more coils that are wound around, disposed within, or more preferably embedded in the shaft 20 and that extend along a length of the shaft 20. In an exemplary embodiment, two coils 20a, 20b extend through the shaft 20 in opposite directions such that the coils 20a, 20b are cross-wound, as shown. The pitch of the coils 20a, 20b, as well as the materials used to form the coils 20a, 20b, can vary to obtain a desired torsional strength. In one exemplary embodiment, the pitch of each coil 20a, 20b can be less than 90°.

The pitch of the threads 20t on the distal end 20d of the elongate shaft 20 can also vary. FIG. 2B illustrates a distal end 20d' of the elongate shaft 20' having threads 20t' formed thereon with a single or constant pitch. In another embodiment, shown in FIG. 2C, the thread pitch can vary. For example, the distal end 20d'' can include a distal-most portion 20a'' having a first thread pitch, and an adjacent proximal portion 20b'' having a second thread pitch that is greater than the first thread pitch. As a result, the first thread pitch will allow for a quick attachment to the end effector, while the second thread pitch will provide fine control over movement of the end effector relative to the elongate shaft. This can be particularly advantageous where the engagement mechanism is used for both attachment/detachment of the end effector, and actuation, e.g., translation of the end effector relative to the shaft.

In another embodiment, multiple shafts can be used to engage the end effector. For example, FIG. 2D illustrates two shafts 26, 28, each having threads 26t, 28t formed thereon, for mating with threads 27t, 29t formed in corresponding lumens or bores 27, 29 in the end effector 25. While not shown, the two shafts 26, 28 can be housed within and extend through an outer shaft of the device. In use, the two shafts 26, 28 can be used to engage a single end effector 25 as shown, or two separate end effectors. The shafts 26, 28 can also be used to actuate the end effector 25, or portions thereof. In other embodiments, where the end effector 25 is a bipolar device, each shaft 26, 28 can be used to carry the current.

Figure 3A:
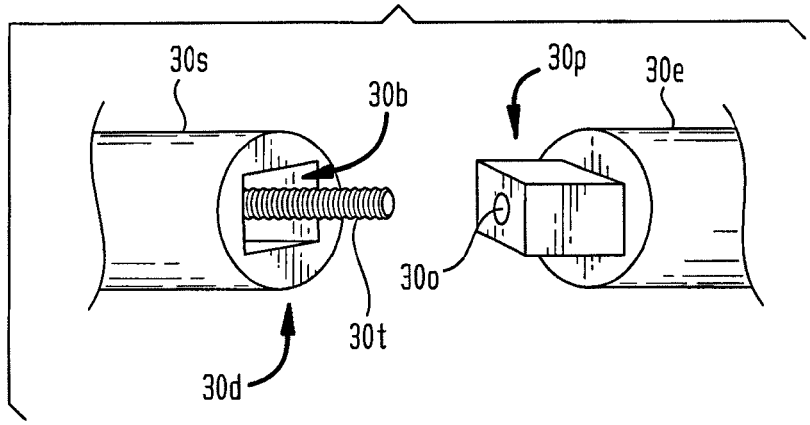
FIG. 3A is a side perspective view of an engagement mechanism that utilizes threads and an asymmetrical anti-rotation mechanism according to another embodiment.

In other embodiments, shown in FIGS. 3A-3E, the threaded engagement mechanism can also include an anti-rotation feature to prevent undesired rotation of the end effector during use of the device. FIG. 3A illustrates one embodiment of an anti-rotation feature in the form of an asymmetrical mating element. In particular, the distal end 30d of the elongate shaft 30s can include a bore or lumen 30b formed therein and having an asymmetrical shape, such as a square shape. The proximal end 30p of the end effector 30e can have a complementary shape that is adapted to be received within the bore 30b formed in the elongate shaft 30s. As shown in FIG. 3A, the proximal end 30p of the end effector 30e has a square shape that fits within the square bore 30b in the shaft 30s. While the shape can be complementary, the surfaces do not need to be congruent. For example, they can include cut-outs etc. As further shown, a threaded shaft 30t can extend through the lumen 30b in the elongate shaft 30s and it can extend into a threaded bore 30o formed in the proximal end 30p of the end effector 30e. In use, as the threaded shaft 30t is rotated into the threaded bore 30o formed in the end effector 30e to mate the end effector 30e to the elongate shaft 30s, the square proximal end 30p of the end effector 30e will be pulled into the square bore 30b in the elongate shaft 30s to thereby prevent undesired rotation of the end effector 30e relative to the shaft 30s during use of the device. A person skilled in the art will appreciate that the bore in the elongate shaft and the proximal end of the end effector can have a variety of other shapes, such as rectangular, hexagonal, oval, etc., to prevent rotation of the end effector relative to the elongate shaft. Moreover, the asymmetrical bore can be formed in the end effector, and the outer surface of the elongate shaft can be shaped to be received within the bore.

Figure 3B:
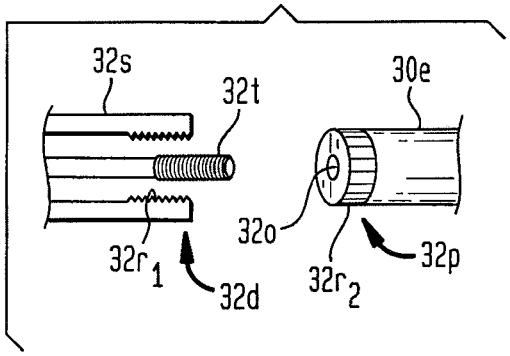
FIG. 3B is a side view of another embodiment of an engagement mechanism that uses threads and surface features to prevent rotation.

FIG. 3B illustrates another embodiment of an anti-rotation mechanism for use with a threaded engagement mechanism. In this embodiment, the distal end 32d of the elongate shaft 32s and the proximal end 32p of the end effector 32e include surface features formed thereon or therein to prevent rotation of the two components relative to one another. In particular, the distal end 32d of the elongate shaft 32e includes a series of ridges $32r_1$ formed around an inner surface thereof, and the proximal end 32p of the end effector 32e includes corresponding ridges $32r_2$ formed around an outer surface thereof. In use, a threaded shaft 32t extending through the elongate shaft 32s can be threaded into a corresponding threaded bore 32o formed in the end effector 32e. As the elongate shaft 32s is advanced over the proximal end 32p of the end effector 32e, the surface features $32r_1$, $32r_2$ will engage one another to prevent rotation of the end effector 32e relative to the elongate shaft 32s.

Figure 3C:
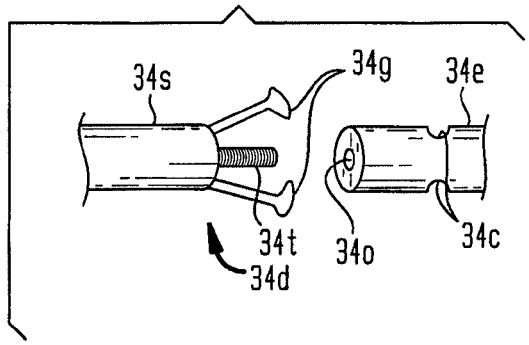
FIG. 3C is a side view of yet another embodiment of an engagement mechanism that uses threads and graspers to prevent rotation.

In another embodiment, shown in FIG. 3C, the distal end 34d of the elongate shaft 34s can include a grasping element formed thereon for grasping the end effector 34e to prevent rotation of the end effector 34e during use of the device. As shown, the grasping element is in the form of opposed arms 34g that are pivotally coupled to the distal end 34d of the elongate shaft 34s. The arms 34g can be moved toward one another to engage corresponding detents 34c formed in an outer surface of the end effector 34e, thereby engaging the end effector 34e. Various techniques known in the art can be used to move the arms 34g between the open and closed positions including, for example, one or more cables having a distal end coupled to the arms and a proximal end coupled to a trigger formed on a handle of the device. Actuation of the trigger can pull the cables, thereby pulling the arms 34g toward or away from one another. Alternatively, the arms 34g can be biased to a closed configuration to engage the end effector 34e as the elongate shaft 34s is advanced over the end effector 34e. In use, a threaded shaft 34t extending through the elongate shaft 34s can be threaded into a threaded bore 34o formed in the end effector 34e. As the end effector 34e is pulled toward the elongate shaft 34s, the opposed arms 34g can close or be closed to engage the detents 34c, thereby preventing rotation of the end effector 34e relative to the elongate shaft 34s.

Figure 3D:
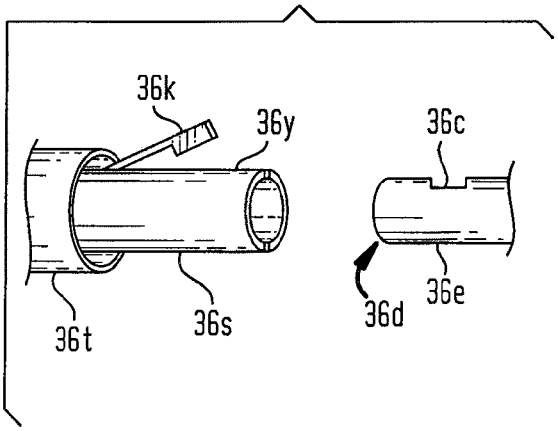
FIG. 3D is a side view of an engagement mechanism that uses threads and a pawl to prevent rotation according to another embodiment.

In yet another embodiment, a pawl 36x can be used to engage the end effector 36e to prevent rotation of the end effector 36e relative to the elongate shaft 36s during use of the device. As shown in FIG. 3D, the pawl 36x is pivotally coupled to the distal end of the elongate shaft 36s, and the end effector 36e includes a cut-out or detent 36c formed on an outer surface thereof for receiving the pawl 36x. In use, the elongate shaft 36s can be advanced over and rotated relative to the end effector 36e such that threads (not shown) formed within the elongate shaft 36s engage corresponding threads (not shown) formed on an outer surface of the end effector 36e. Once the pawl 36x is positioned adjacent to the cut-out 36c, the pawl 36x will extend through an elongate slot 36y formed in the shaft 36s and it will extend into and engage the cut-out 36c in the end effector 36e, thereby preventing rotation of the end effector 36e relative to the elongate shaft 36s. In one embodiment, the pawl 36x can be spring-loaded to bias the pawl 36x toward and into the cut-out 36c. As the elongate shaft 36s is threaded over the end effector 36e, the pawl 36x will extend through the slot 36y and slide along the end effector 36e eventually extending into the cut-out 36c formed in the outer surface of the end effector 36e. The biasing mechanism can be configured to allow the pawl 36x to be released from the cut-out 36c when a significant force is applied thereto, i.e., by rotating the elongate shaft 36s in an opposite direction to release the end effector 36e. Alternatively, rather than having a spring-loaded pawl 36x, an actuator can be used to move the pawl 36x between an initial position and an engaged position in which the pawl 36x engages the cut-out 36c. The actuator can be, for example, a tube that is slid over the pawl 36x or a cable or wire that is coupled to the pawl 36x and that moves the pawl 36x relative to the elongate shaft 36s.

Figure 3E:
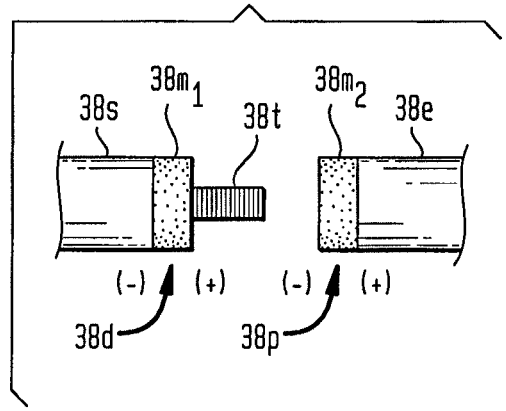
FIG. 3E is a side view of another embodiment of an engagement mechanism that uses threads and a magnet to prevent rotation.

In yet another embodiment, one or more magnets can be used to prevent rotation of the elongate shaft relative to the end effector. As shown in FIG. 3E, the distal end 38d of the elongate shaft 38s includes a magnet $38m_1$ mated thereto, and the proximal end 38p of the end effector 38e includes a corresponding magnet $38m_2$ mated thereto. The magnets $38m_1$, $38m_2$ have opposite polarities to allow the magnets $38m_1$, $38m_2$ to magnetically engage one another when the elongate shaft 38s is positioned in proximity to the end effector 38e. In use, as a threaded shaft 38t extending through the elongate shaft 38s is threaded into a corresponding threaded bore (not shown) formed in the end effector 38e, the magnets $38m_1$, $38m_2$ will engage one another to thereby prevent undesired rotation of the end effector 38e relative to the elongate shaft 38s during use of the device.

Figure 4A:
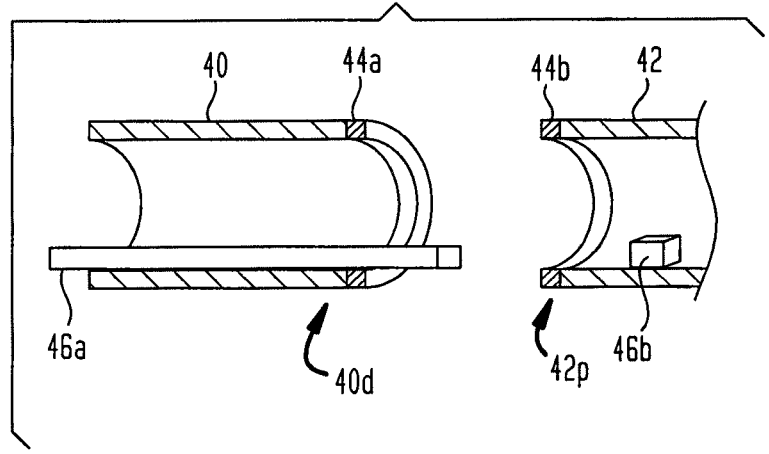
FIG. 4A is a side cross-sectional view of yet another embodiment of an engagement mechanism having a magnet for attachment and a pusher for detachment.
Figure 4B:
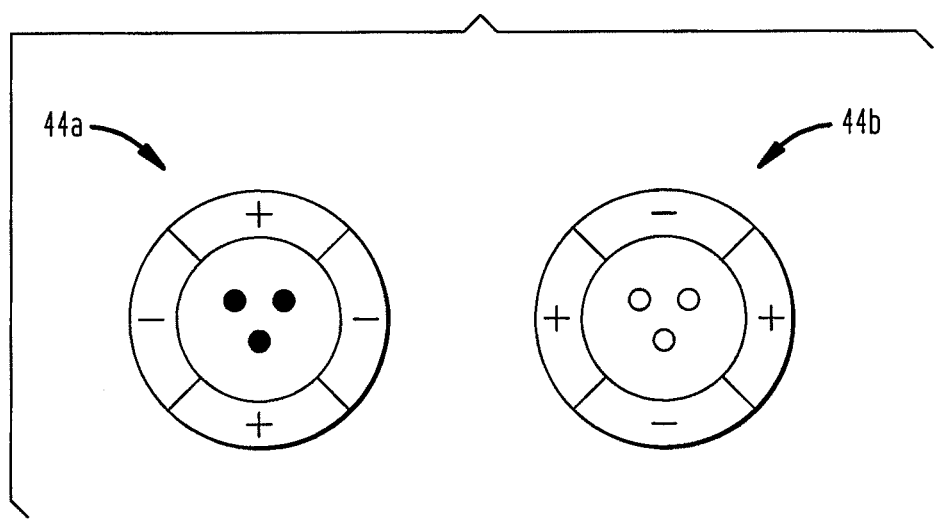
FIG. 4B is a cross-sectional view of the magnets of FIG. 4A having alignment features.

FIG. 4A illustrates another embodiment of an engagement mechanism for performing different actions, such as attachment/detachment and axial translation (push/pull). In this embodiment, the engagement mechanism includes two components: an attachment mechanism and a detachment mechanism. The attachment mechanism is in the form of a magnet 44a that is disposed around a distal end 40d of a shaft 40s and a corresponding magnet 44b of opposite polarity disposed around the proximal end of the end effector 42. The magnets 44a, 44b on the shaft 40s and end effector 42 can have various configurations depending on the configurations of the shaft 40s and end effector 42. As shown in FIG. 4A, the shaft 40s and end effector 42 each have a generally elongate hollow cylindrical configuration, and thus the magnets 44a, 44b have a generally cylindrical configuration with a bore extending therethrough and aligned with an inner lumen of the shaft 40s and end effector 42. The magnets 44a, 44b can be mated to the shaft 40s and end effector 42 using various techniques known in the art, including adhesives, a threaded connection, etc. The magnets 44a, 44b can also optionally be configured to axially align the elongate shaft 40s with the end effector 42. For example, each magnet 44a, 44b can be constructed with multiple alternating polarities. FIG. 4B illustrates each magnet 44a, 44b having four polarities that alternate around the perimeter thereof. Thus, when the end effector 42 and elongate shaft 40s are placed into proximity with each other, the opposite polarities will align with one another to thereby axially align the end effector 42 and the shaft 40s. Returning back to FIG. 4A, the detachment mechanism is in the form of a pusher 46a that is slidably disposed within the shaft 40s, and an abutment or protrusion 46b that is formed on an inner surface of the end effector 42. The pusher 46a can be, for example, a generally elongate rod that extends through the length elongate shaft 40s to allow a user to grasp a proximal end of the pusher 46a and slidably move the pusher 46a relative to the elongate shaft 40s. In use, the magnet 44A on the distal end 40d of the shaft 40s can be positioned adjacent to the end effector 42 to be attached thereto. The two magnets 44a, 44b will engage one another to mate the end effector 42 to the shaft 40s. In order to release the end effector 42 from engagement with the shaft 40s, the pusher 46a can be advanced distally through the shaft 40s and into the end effector 42 to abut against the protrusion 46b formed within the proximal end of the end effector 42. The pusher 46a can thus push the end effector 42 away from and out of engagement with the shaft 40s, thereby releasing the end effector 42. A person skilled in the art will appreciate that other techniques can be used to detach the end effector 42 from the shaft 40s. For example, the end effector 42 could be positioned adjacent to a tissue wall and the shaft 40s could be manipulated to force the end effector 42 to detach from the shaft 40s.

Figure 5A:
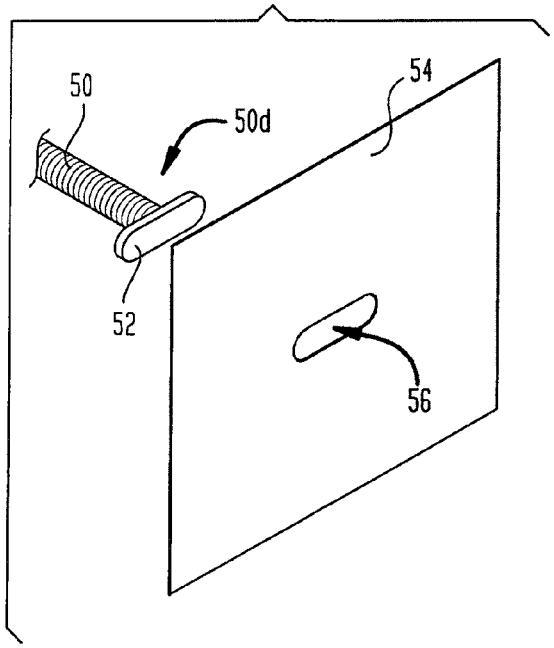
FIG. 5A is a perspective view of another embodiment of an engagement mechanism having male and female members, showing the male member about to be inserted through the female member.

FIGS. 5A-7C illustrate other exemplary engagement mechanisms used to perform different actions, such as attachment/detachment and axial translation (push/pull). In these embodiments, the engagement mechanisms utilize a male/female mating connection. Turning first to FIGS. 5A-5B, the engagement mechanism is in the form of a male member 52 disposed on a distal end 50d of an elongate shaft 50, and a corresponding female member 56 formed within a wall 54. While not shown, the elongate shaft 50 can be slidably disposed through an outer shaft of the device, and the wall 54 can be formed on or within an end effector. The particular shape of the male and female members can vary, but in the illustrated embodiment the male member 52 has a generally elongate rectangular shape, and the female member 56 is in the form of a complementary rectangular bore. While the shape of the male and female members may be complementary, the surfaces do not need to be congruent. The male and female members can include cut-outs or other features. In use, the male member 52 can be aligned with and advanced through the female member 56 in the wall 54, as shown in FIG. 5B. Once positioned through the female member 56, the male member 52 can be rotated, e.g., 90°, relative to the female member 56, thereby locking the male and female members 52, 56 as shown in FIG. 5C. A person skilled in the art will appreciate that the male and female members can have a variety of other shapes and sizes.

Figure 6A:
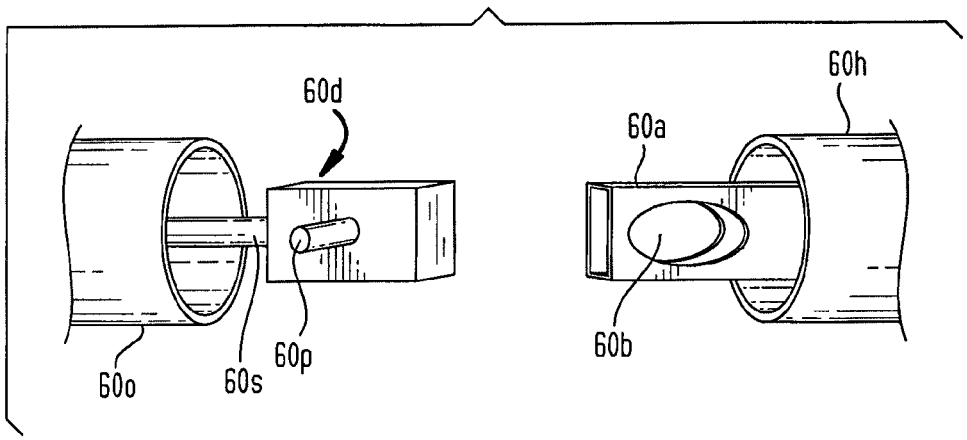
FIG. 6A is a perspective view of another embodiment of an engagement mechanism that uses a pin and bore connection.

FIG. 6A illustrates another embodiment of a male and female mating element. In this embodiment, the male member is in the form of a pin 60p and the female member is in the form of a bore 60b. In particular, the male pin 60p is formed on and extends laterally outward from a body located on a distal end 60d of a shaft 60s. The shaft 60s can be slidably disposed through an outer shaft 60o of the device. The female bore 60b is also formed in and extends laterally through a body located on a proximal end of a shaft 60s. The shaft 60s can be coupled to and disposed within an outer shaft or housing 60h of the end effector 60e. In use, the male pin 60p is positioned through the bore 60b, and the outer shaft 60o is advanced over the bodies and toward the outer shaft or housing 60h of the end effector 60e, thereby engaging the bodies to prevent the pin 60p from being removed from the bore 60b. To release the end effector 60e, the outer shaft 60o can be retracted relative to the end effector 60e, thereby allowing the pin 60p to be released from the bore 60b.

Figure 6B:
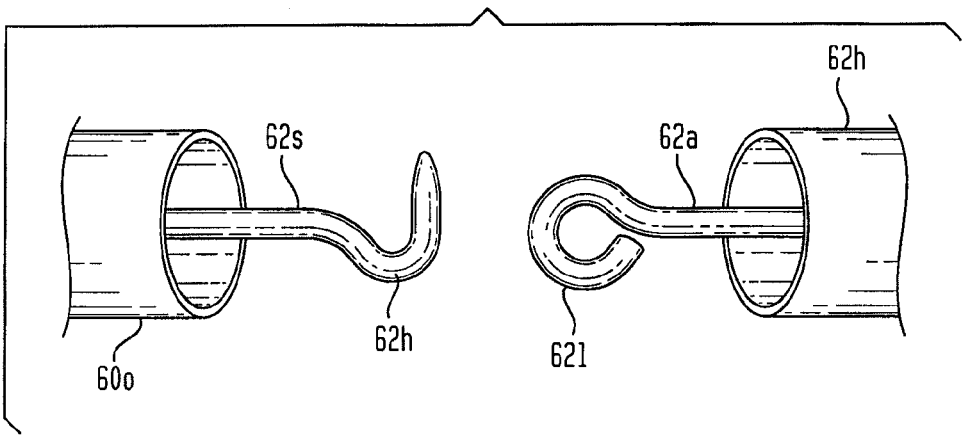
FIG. 6B is a perspective view of an engagement mechanism that uses a hook and loop connection according to another embodiment.

In a similar embodiment, shown in FIG. 6B, the pin and bore can be replaced with a hook 62h and loop 62l. In particular, a male hook 62h can be formed on a distal end of an elongate shaft 62s extending through an outer shaft 62o, and a female loop 62l can be formed in a proximal end of an elongate shaft 62a extending through an outer shaft or housing 62h of the end effector. In use, the hook 62h can be positioned to engage the loop 62l, thereby mating the end effector to the elongate shaft 62s. The outer shaft 62o can optionally be advanced over the hook and loop 62h, 62l once mated to prevent detachment of the hook and loop 62h, 62l until desired.

Figure 6C:
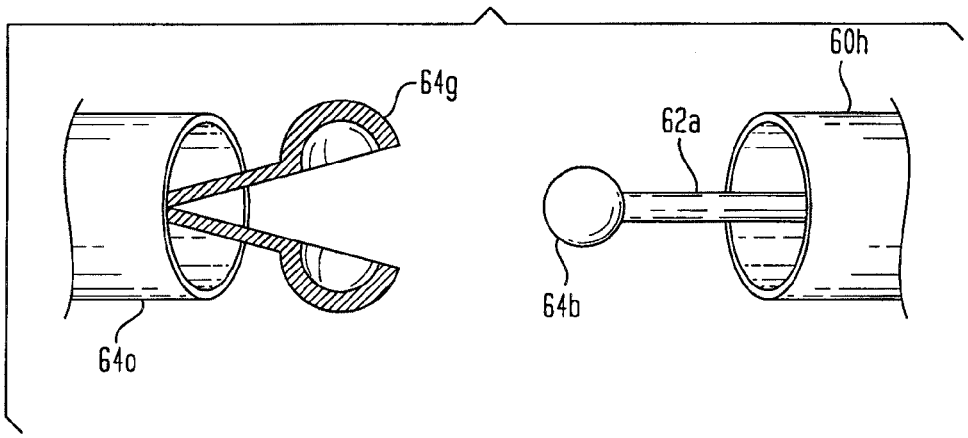
FIG. 6C is a perspective view of a ball and grasper engagement mechanism according to yet another embodiment.

In another embodiment, a ball and grasper can be used. FIG. 6C illustrates opposed grasper arms 64g extending from a distal end of an outer shaft 64o, and a ball 64b formed on a proximal end of a shaft 64a extending proximally from an outer shaft or housing 64h of the end effector. The grasper arms 64g can be positioned around the ball 64b, and the outer shaft 64o can be advanced distally over the grasper arms 64g to close the arms 64g and thereby cause the arms 64g to engage the ball 64b. In the closed position, the grasper can control movement of the end effector in various directions including axial rotation and translation. To release the end effector from the shaft 64o, the outer shaft 64o can be moved proximally thus allowing the grasper arms 64g to open up and release the ball 64b.

Figure 7A:
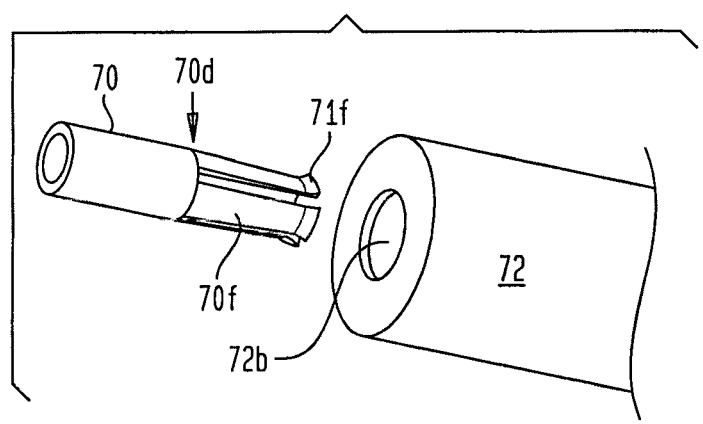
FIG. 7A is a perspective view of yet another embodiment of an engagement mechanism having expanding fingers for engage a bore.
Figure 7B:
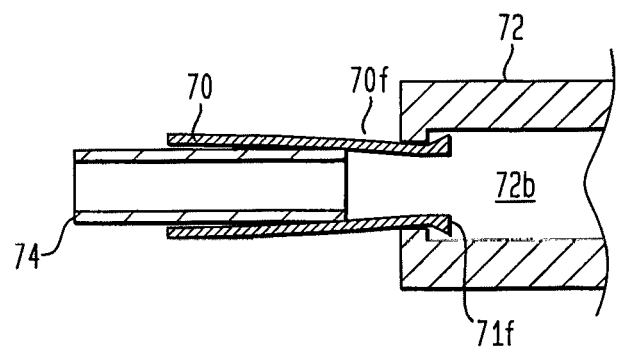
FIG. 7B is a cross-sectional view of the engagement mechanism of FIG. 7A showing the expanding fingers inserted into the bore.
Figure 7C:
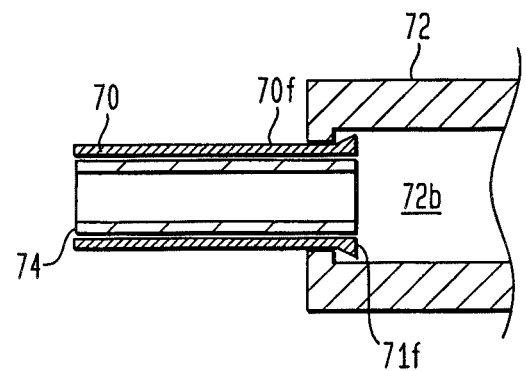
FIG. 7C is a cross-sectional view of the engagement mechanism of FIG. 7C showing an inner shaft inserted into the expanding fingers to lock the fingers in the bore.

FIGS. 7A-7B illustrate another embodiment of an engagement mechanism in the form of deflectable fingers. In this embodiment, the distal end 70d of the elongate shaft 70 includes several deflectable fingers 70f formed therearound. The fingers 70f can be formed by cutting one or more longitudinally oriented slots in the shaft 70. Each finger can also include a flange 71f formed on an outer surface of a distalmost end thereof. The end effector 72 can include a bore 72b formed therein and configured to receive the fingers 70f. In use, the fingers 70f can be biased to a closed configuration, in which they are sized to be received within the bore 72*b* in the end effector 72. Once disposed through the bore 72*b*, as shown in FIG. 7B, an expander element, such as an inner shaft 74, can be advanced through the elongate shaft 70 to thereby expand the fingers 70*f* radially outward. As a result, the flanges 71*f* on the fingers 70*f* will engage the wall that surrounds the bore 72*b*, as shown in FIG. 7C, thereby preventing removal of the fingers 70*f* from the end effector 72. To release the end effector 72 from the shaft 70, the inner shaft 74 can be moved proximally to allow the fingers 70*f* to collapse toward one another and thus be pulled out through the bore 72*b*.

Figure 8:
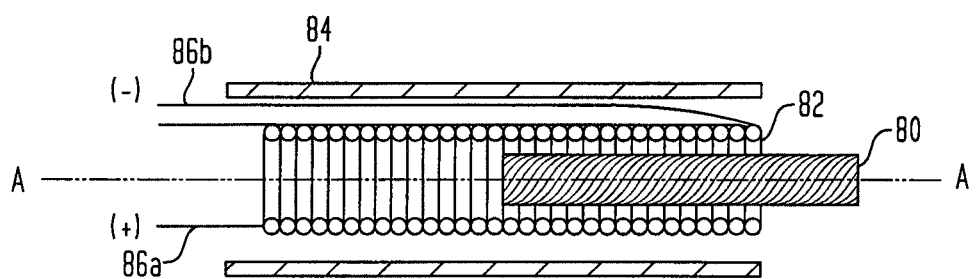
FIG. 8 is a cross-sectional view of another embodiment of an engagement mechanism that utilizes an electromagnetic connection.

FIG. 8 illustrates another exemplary embodiment of an engagement mechanism for performing various actions, such as attachment/detachment and/or actuation. In this embodiment, the engagement mechanism utilizes electromagnetic energy to effect a desired action. In particular, the engagement mechanism is in the form of a magnetic shaft 80 (or a shaft which contains a ferromagnetic material such as iron) that is housed within an electromagnetic coil 82. The electromagnetic coil 82 can be disposed within a distal portion of an outer elongate shaft 84, which is preferably formed from an insulative material. The configuration of the coil 82 can vary, but in an exemplary embodiment the coil 82 is configured to produce a magnetic field when energy is delivered thereto. The length and size of the coil 82 can vary depending on the strength of the magnetic field needed to actuate the magnetic shaft 80. In order to deliver energy to the coil 82, first and second electrical leads 86*a*, 86*b* can be coupled to the coil 82. In the illustrated embodiment, a positive lead 86*a* is coupled to a proximal end of the coil 82, and a negative lead 86*b* is coupled to a distal end of the coil 82. The leads 86*a*, 86*b* can be standard conductive wires having an insulative coating disposed there over, and they can extend through the outer shaft 84, be embedded within the walls of the outer shaft 84, or extend along an external surface of the outer shaft 84.

In use, when energy is delivered to the coil 82 the generated magnetic field applies a force to the magnetic shaft 80, causing the magnetic shaft 80 to translate along a longitudinal axis A of the device. The direction of movement, which is controlled by the direction of current flow through the coil 82, can vary depending on the desired action to be performed. For example, in one embodiment the magnetic shaft 80 can be configured to perform the action of attaching and detaching an end effector to and from the distal end of the outer shaft 84. In particular, the distal end of the magnetic shaft 80 can be configured to magnetically engage a magnet formed on a proximal end of an end effector to thereby attach the end effector to outer 84. In this embodiment, energy activation is thus preferably effective to translate the magnetic shaft 80 distally relative to the outer shaft 84 to cause the distal end of the magnetic shaft 80 to extend a distance beyond a distal end of the outer shaft 84. The distal end of the magnetic shaft 80 can thus be positioned adjacent to and engage the magnet formed on the end effector. When energy delivery is terminated, the magnetic shaft 80 will move proximally such that it is retracted within the outer shaft 84. As a result, the magnetic shaft 80 will disengage from the end effector, thereby releasing the end effector from the outer shaft 84. A second end effector can then be attached to the device if necessary.

In another embodiment, the distal end of the magnetic shaft 80 can be configured to perform other actions, such as translating a portion of an end effector to open and close jaws, move a cutting element, advance a clip or staple, etc. For example, where the end effector includes opposed jaws that are pivotally coupled to one another, the magnetic shaft 80 can be configured to magnetically engage a magnet formed on a clevis that is coupled to one or both of the jaws. When energy is delivered to the coil 82, the magnetic shaft 80 can translate in a first direction, e.g., proximally within the outer shaft 84, to pull the clevis proximally thereby moving the jaws to a first position, e.g., a closed position. When energy delivery is terminated, the magnetic shaft 80 will translate in an opposite direction, e.g., distally within the outer shaft 84, to push the clevis distally, thereby moving the jaws to a second position, e.g., an open position. Depending on the configuration of the end effector, an alternating current can also optionally be used to continuously translate the magnetic shaft 80 proximally and distally. A person skilled in the art will appreciate that, where the electromagnetic engagement mechanism is used to perform an action other than attachment and detachment of the end effector to and from the outer shaft, a second engagement mechanism is preferably provided to perform the action of attachment and detachment.

Figure 9:
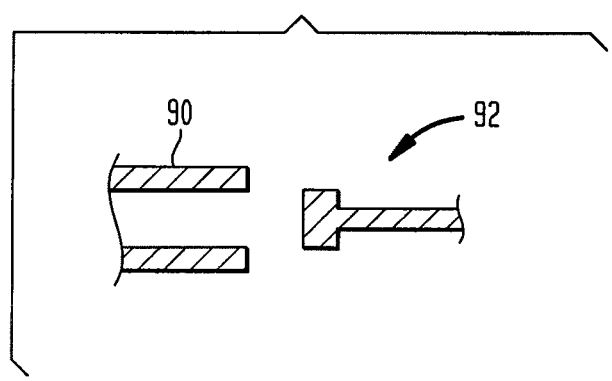
FIG. 9 is a cross-sectional view of yet another embodiment of an engagement mechanism that uses pressure.

FIG. 9 illustrates yet another embodiment of an engagement mechanism. In this embodiment, the engagement mechanism utilizes pressure. In particular, the elongate shaft 90 can be coupled to a pneumatic or hydraulic pressure actuator for generating a force within the elongate shaft 90. The end effector can include a piston 92 formed on a proximal end thereof and adapted to be received within the elongate shaft 90. In use, the pneumatic or hydraulic pressure actuator can be activated to move the piston 92 proximally and distally relative to the elongate shaft 90. This is particularly advantageous for use in actuating an end effector. A separate engagement mechanism can be providing for attaching and detaching the end effector to the elongate shaft.

As indicated above, the various engagement mechanisms can be used in any combination to perform various actions, such as attachment/detachment, and actuation, including axial translation (push/pull movement), and axial rotation. FIGS. 10A-19 illustrate various exemplary devices that utilize one or more of the above-described engagement mechanisms to attach/detach and/or actuate an end effector.

Figure 10A:
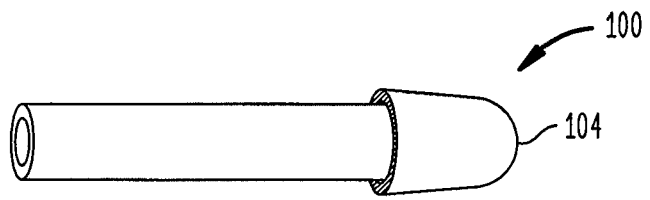
FIG. 10A is a side perspective view of one embodiment of an end effector in the form of a needle.
Figure 10B:
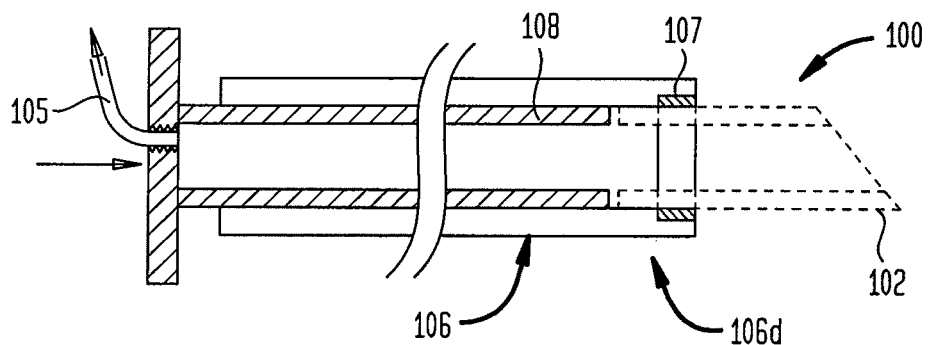
FIG. 10B is a cross-sectional view of the needle of FIG. 10A, showing the needle mated to a shaft using a magnetic engagement mechanism.
Figure 10C:
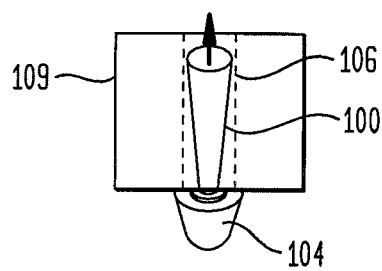
FIG. 10C is a cross-sectional view of the needle and shaft of FIG. 10A, showing the needle and shaft being retracted into an endoscope to remove an end cap disposed over the tip of the needle.

FIGS. 10A-10C illustrate an end effector in the form of a surgical needle 100. The surgical needle 100 has a generally elongate hollow configuration with a sharp tissue-penetrating tip 102. A protective cap 104 can be disposed over the tissue-penetrating tip 102 so as to prevent undesired penetration of tissue prior to attaching the needle 100 to a shaft. Thus, with the protective tip 104, the needle 100 can be introduced into a body cavity and can float in the body cavity until it is ready for use. While any of the various engagement techniques previously described can be used, in this embodiment the needle 100 uses a magnetic engagement and a pusher similar to that previously described with respect to FIG. 4A to attach and detach the needle. In particular, the needle 100 can be formed from a magnetic material, such as a ferromagnetic material, and the distal end 106*d* of the shaft 106 can include a magnet 107 disposed therein for mating to the needle 100. While the position of the magnet 107 on the shaft 106 can vary, in the illustrated embodiment the magnet 107 is disposed around and recessed within the distal end 106*d* of the shaft 106. Thus, the shaft 106 can be guided to position the shaft 106 around the proximal end of the needle 100, thereby attaching the needle 100 to the shaft 106. Once attached, the protective cap 104 can be removed by advancing an outer shaft, such as an endoscope 109 over the shaft 106, or retracting the shaft 106 relative to an endoscope 109 through which the shaft 106 is inserted, to push the protective cap 104 off of the needle 100, as shown in FIG. 10C. The needle can then be used to inject materials into the body and/or to puncture tissue, for example, through port 105. When the procedure is complete, an inner sheath or pusher 108 disposed within the shaft 106 can be advanced distally to abut the proximal end of the needle 100 and thereby push the needle 100 out of the shaft 106 to detach the needle 100. Prior to detachment, the shaft 106 can optionally be manipulated to insert the needle 100 back into the protective cap 104, which is floating in the body lumen. Alternatively, the shaft 106 can be removed through the endoscope 109 with the needle 100 attached thereto so that the needle 100 does not need to remain in the body.

FIGS. 11A-11B illustrates another embodiment of an end effector in the form of a snare 110. The snare 110 utilizes the ball and grasper engagement mechanism previously discussed with respect to FIG. 6C to attach and detach the snare 110 to the shaft 112 and to actuate the snare 110. As shown, the snare 110 is in the form of a wire that is shaped into a snare loop and that includes two ends that are mated to one another and that have a ball 110b mated thereto. The shaft 112 includes a grasper 114 extending therethrough with opposed arms 114a, 114b on the distal end that are biased toward an open configuration. When the grasper 114 is advanced distally beyond a distal end of the shaft 112, the arms 114a, 114b are open and can be positioned around the ball 110b on the snare 110. The shaft 112 can then be advanced distally over the grasper arms 114a, 114b to bring the arms 114a, 114b together, thereby causing the arms 114a, 114b to engage the ball 110b and thus attach the snare 110 to the shaft 112, as shown in FIG. 11B. Once attached, the grasper 114 can be moved proximally and distally within the shaft 112 to open and close the snare loop.

Figure 12A:
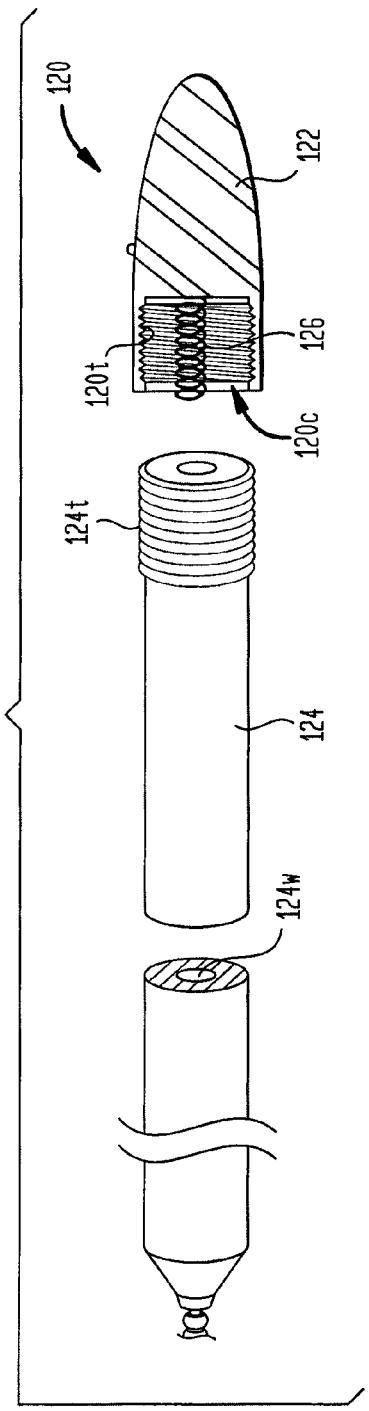
FIG. 12A is a side partially cross-sectional view of another embodiment of an end effector in the form of a monopolar probe that uses a threaded engagement mechanism.
Figure 12B:
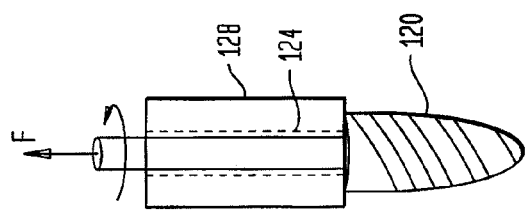
FIG. 12B is a side partially cross-sectional view of the monopolar probe of FIG. 12A showing the probe being retracted into an endoscope to generate a counter torque to allow a shaft to be unthreaded from the probe.

FIGS. 12A and 12B illustrate a monopolar probe end effector 120 having a threaded engagement mechanism for attachment and detachment. In general, the monopolar probe 120 has an elongate shape with at least one active electrode 122 disposed therearound. FIGS. 12A and 12B illustrate the electrode 122 coiled around the probe 120. A proximal end of the probe 120 includes a cavity 120c formed therein and having threads 120t for mating with corresponding threads 124t on a distal end of a shaft 124. The threaded engagement mechanism is similar to that previously described with respect to FIG. 2A. In use, the distal end of the shaft 124 can be manipulated and rotated to thread the distal end into the cavity 120c formed in the probe 120, thereby mating the probe 120 to the shaft 124. In order to deliver energy to the electrode 122, the probe 120 and shaft 124 can include electrical connectors. While various electrical connectors can be used, FIG. 12A illustrates a conductive spring 126 disposed within the cavity 120c in the probe 120 and in electrical communication with the active electrode 122. A conductive material, such as a wire 124w or other member, can extend through the shaft 124 and it can be positioned such that, when the shaft 124 and probe 120 are mated, the conductive wire 124w comes into contact with the conductive spring 126. The spring 126 can be compressed within the cavity 120c as the probe 120 and shaft 124 are mated to ensure contact between the two components. Once connected, energy can be delivered through the conductive wire 124w to the spring 126 and thus to the electrode 122, thereby allowing the probe 120 to be used to ablate or otherwise treat tissue. Once the procedure is complete, the probe 120 can be removed from the shaft 124 by unthreading the shaft 124 from the probe 120. In an exemplary embodiment, the probe 120 has an outer diameter that is greater than an outer diameter of the shaft 124 to allow the probe 120 to abut against a distal end of an outer sheath 128, such as an endoscope, when the shaft 124 is retracted, as shown in FIG. 12B. Friction will thus be generated between the proximal end of the probe 120 and the outer sheath 128 to provide counter torque as the shaft 124 is rotated and unthreaded from the probe 120. In other embodiments, an insulated electrode path can extend to an exterior portion of an end effector to enable the end effector to contact tissue and allow the application of radio frequency energy to the tissue using a conventional cautery tool. The end effectors can also be configured to deliver other forms of energy, such as microwave and ultrasonic energy.

FIG. 13A illustrates a bipolar probe end effector 130 having a magnetic engagement mechanism and pusher for attaching and detaching the probe to and from the shaft. In general, the bipolar probe 130 is similar to the monopolar probe but includes two electrodes 132a, 132b disposed therearound. Each electrode 132a, 132b can include a proximal end 133a, 133b that extends proximally from the probe 130. The shaft 134 can include two conductive members or leads 136a, 136b extending therethrough for delivering energy to each electrode 132a, 132b. The leads 136a, 136b can extend into two bores 137a, 137b formed in the distal end of the shaft 134 for receiving the proximal ends 133a, 133b of the electrodes 132a, 132b, a shown in FIG. 13B. Thus, when the electrodes 132a, 132b are inserted into the bores 137a, 137b the electrodes 132a, 132b will contact the leads 136a, 136b, thereby electrically connecting the probe 130 to the shaft 134. In order to mate the probe 130 to the shaft 134, FIG. 13A illustrates a magnet 138a disposed on the distal end of the shaft 134 and a magnet 138b disposed on the proximal end of the probe 130. In order to align the probe 130 with the shaft 134 so as to cause the electrodes 132a, 132b to extend into the bores 137a, 137b and mate to the leads 136a, 136b, the magnets 138a, 138b can have a configuration as previously described with respect to FIG. 4B. Once mated, the probe 130 can be used to perform various surgical procedures. When the procedure is complete, the shaft 134 can include a pusher 139 extending therethrough and adapted to be advanced distally to push the probe 130 off of and out of magnetic engagement with the shaft 134.

FIGS. 14A and 14b illustrate another embodiment of an end effector in the form of a clipping device 140. As shown, the clipping device 140 generally includes opposed legs 142a, 142b adapted to receive tissue therebetween, and a locking mechanism 144 adapted to slide over the legs 142a, 142b to close and lock the legs 142a, 142b in a closed position. In this embodiment, the clipping device 140 utilizes an electromagnetic engagement mechanism, such as the engagement mechanism previously described with respect to FIG. 8, for attachment/detachment and for actuation. In particular, the proximal end of the clip includes a magnetic shaft 145, and the distal end of the shaft 146 includes an electromagnetic coil disposed therein. When energy is delivered to the coil, the magnetic shaft 145 is pulled into the shaft 146. A distal housing 146h on the shaft 146 will abut against the locking mechanism 144 to advance the locking mechanism 144 over the legs 142a, 142b, thereby closing the clip 140, as shown in FIG. 14B. Further proximal movement of the magnetic shaft 145 within shaft 146 will cause a frangible portion 145f on the magnetic shaft 145 to break, thereby releasing the clip. The frangible portion 145f can be a weakened region of material formed by altering the physical or chemical structure of the shaft 145.

Figure 15:
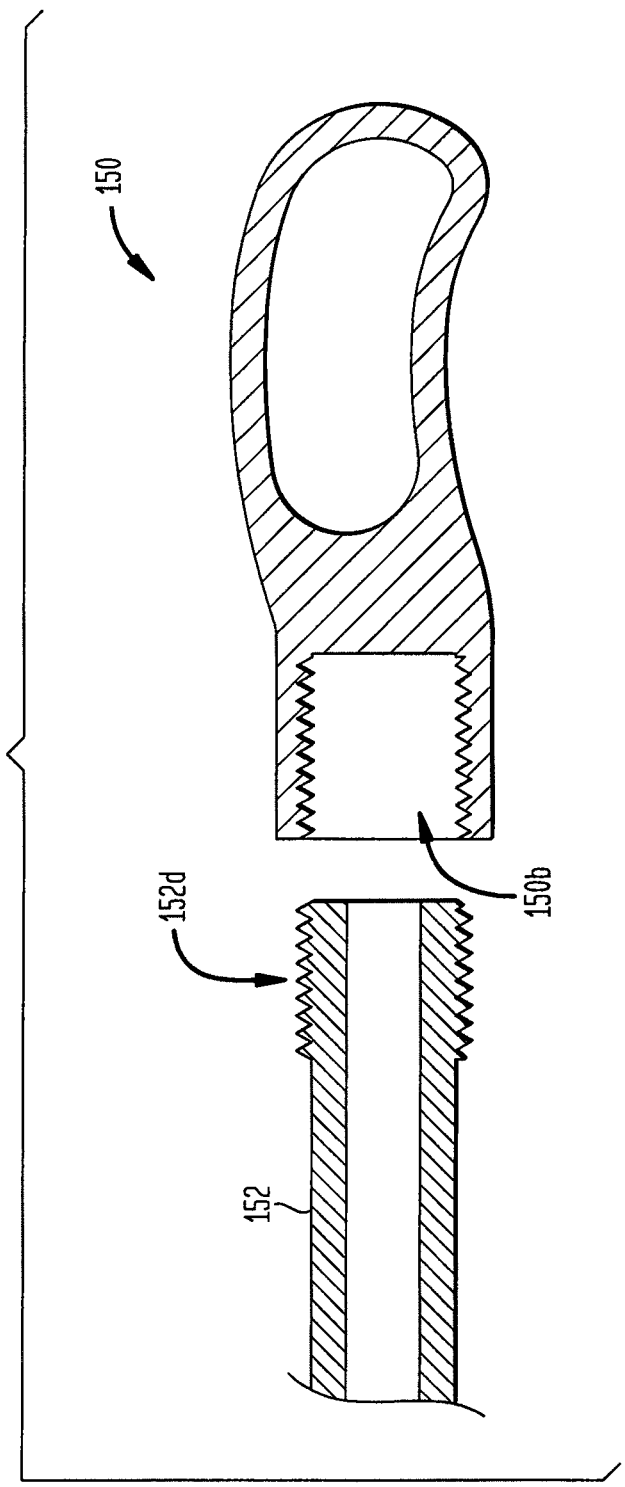
FIG. 15 is a cross-sectional view of an end effector in the form of a retractor that uses a threaded engagement mechanism for mating to a shaft according to yet another embodiment.

FIG. 15 illustrates another embodiment of an end effector in the form of a retractor 150. In this embodiment, the retractor 150 is shown having a pure threaded engagement mechanism, as previously described with respect to FIG. 2A, for attachment/detachment. A threaded distal end 152d of the outer shaft 152 can be inserted into a threaded bore 150b formed in the proximal end of the retractor 150 to mate the retractor 150 to the shaft 152. The shaft 152 can then be manipulated to use the retractor 150 to retract tissue. Once the procedure is complete, the shaft 152 can be unthreaded from the retractor 150. In an exemplary embodiment, the shaft 152 is retracted into an endoscope through which it is disposed such that the proximal end of the retractor 150 abuts against the distal end of the endoscope to create a counter torque as the shaft 152 is unthreaded from the retractor 150.

Figure 16A:
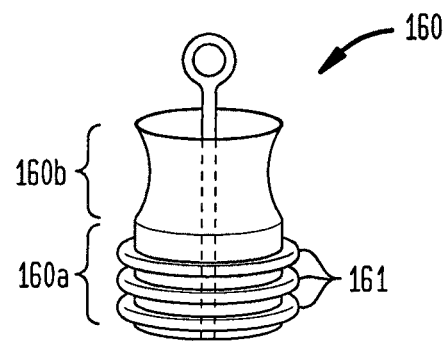
FIG. 16A is a side view of another embodiment of an end effector in the form of a band ligator.
Figure 16B:
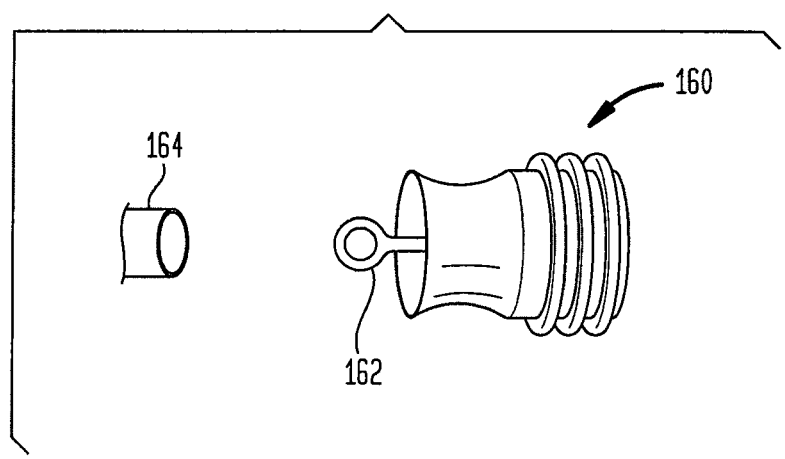
FIG. 16B is a side view of the band ligator of FIG. 16A about to be mated to a shaft using a hook and loop engagement mechanism.
Figure 16C:
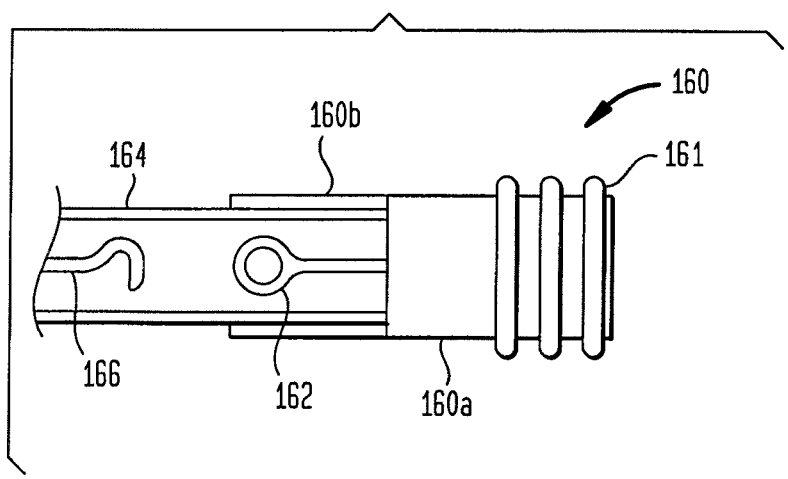
FIG. 16C is a side cross-sectional view of the band ligator and shaft of FIG. 16B mated to one another.

FIGS. 16A-16C illustrates yet another embodiment of an end effector in the form of a band ligator 160. In this embodiment, the band ligator 160 uses a hook and loop engagement mechanism, as previously described with respect to FIG. 6B, for attachment/detachment and for actuation. In particular, the band ligator 160 generally includes a rigid cylindrical section 160a for holding a plurality of elastic bands 161, and an elastic cuff 160b extending from the rigid cylindrical section 160a for mating to the distal end of an elongate shaft 164. The elastic cuff 160b can have a reduced diameter as compared to the cylindrical section 160a to allow the cuff 160b to be received within the distal end of the elongate shaft 164, i.e., an endoscope in the illustrated embodiment. In order to mate the band ligator 160 to the elongate shaft 164, a hook 166 can extend from the distal end of the elongate shaft 164 and it can be manipulated to engage a corresponding loop 162 formed on a proximal end of the band ligator 160. Once engaged, the hook 166 can be retracted into the elongate shaft 164 to pull the elastic cuff 160b into or around the distal end of the elongate shaft 164. The loop 162 can include a proximal end that extends through the cylindrical section 160a and the cuff 160b, and that is threaded through the elastic bands 161. Once the elastic cuff 160b is received in or around the distal end of the shaft 164, further tension applied to the hook 166 will cause the hook 166 to pull the elastic bands 161 distally. When positioned properly, each band 161 can be advanced distally along the cylindrical section until the band 161 is released whereby it engages tissue. In an exemplary embodiment, suction is applied through the shaft 164 and the band ligator 160 to suction tissue to be ligated into the cylindrical portion 160a.

Figure 17:
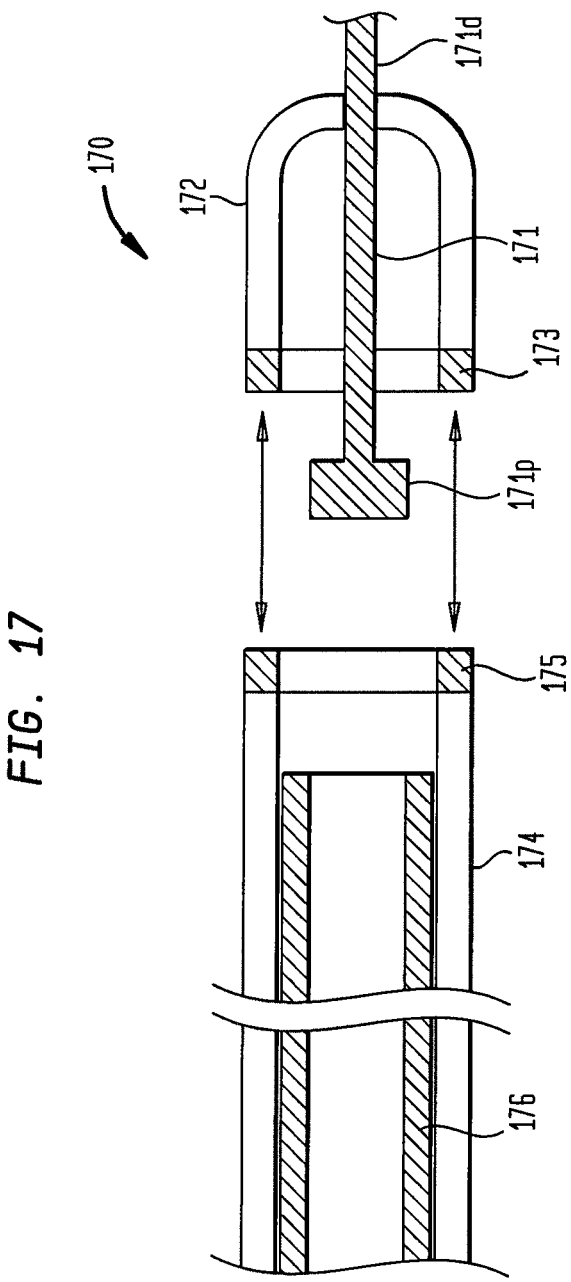
FIG. 17 is a side cross-sectional view of another embodiment of an end effector in the form of a needle knife that uses magnetic and pressure engagement mechanisms.

FIG. 17 illustrates a needle knife end effector 170 that utilizes magnetic and pressure engagement mechanisms for attachment/detachment and actuation, such as those previously described with respect to FIGS. 4A and 9. As shown, the needle knife 170 is in the form of a small diameter wire 171 disposed through a housing or plastic sheath 172. The housing 172 can include a magnet 173 formed on a proximal end thereof for mating with a corresponding magnet 175 formed on a distal end of the shaft 174. The distal end 171d of the wire 171 is configured to cut tissue, and the proximal end 171p of the wire 171 can be sized to be received within a distal end of a sheath 76 disposed within the shaft 174 to permit piston actuation of the needle knife 170. In particular, pneumatic pressure, hydraulic pressure, or other forces can be used to move the needle knife 170 proximally and distally relative to the shaft 174. The sheath 176 can also be conductive to allow energy to be delivered through the sheath 176 and to the needle knife 170.

Figure 5B:
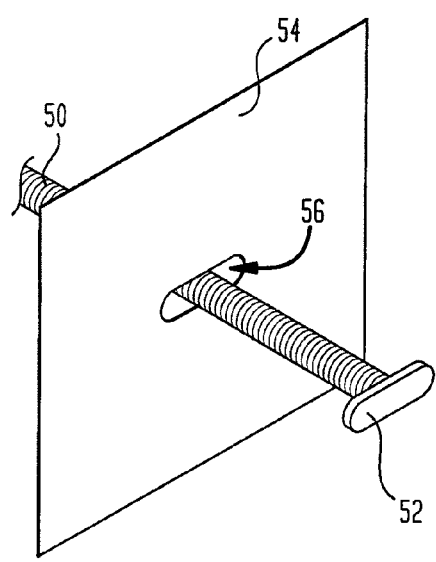
FIG. 5B is a perspective view of the male member of FIG. 5A inserted through the female member.
Figure 5C:
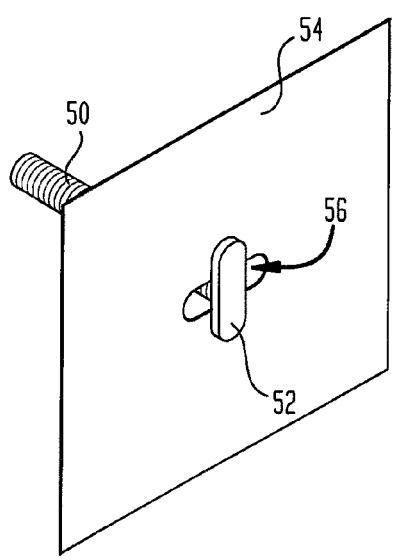
FIG. 5C is a perspective view of the male member of FIG. 5C rotated to lock the male member within the female member.

FIGS. 18A and 18B illustrate yet another embodiment of an end effector having an engagement mechanism that utilizes deflectable fingers for attachment/detachment as previously described with respect to FIGS. 7A-7B, and a male/female engagement mechanism for actuation as previously described with respect to FIGS. 5A-5B. In this embodiment, the end effector is in the form of scissors. As shown, the scissors 180 include first and second cutting jaws 182a, 182b that are pivotally coupled to one another and to a clevis 184. A proximal end of each jaw 182a, 182b is coupled to a connector 183a, 183b that is mated to an actuator sleeve 186 disposed over the clevis 184. The clevis 184 can include a female bore 184a formed therein and having a shape adapted to receive a male member 188m on a distal end of a shaft 188 such that rotation of the male member 188m relative to the female member 184a, as previously described with respect to FIGS. 5A-5B, will lock the clevis 184 to the shaft 188. Once the shaft 188 is mated to the clevis 184, an outer sleeve 189 can be advanced over the shaft 188 to insert deflectable fingers 189f formed on the distal end of the outer sleeve 189 into a proximal end of the actuator sleeve 186 disposed over the clevis 184. An inner shaft 187 can then be advanced distally into the outer sleeve 189 to cause the deflectable fingers 189f to expand outward and engage the actuator sleeve 186. Once mated, the shaft 188 can be moved proximally and distally to move the clevis 184 proximally and distally, thereby opening and closing the jaws. While not shown, the clevis 184 can optionally be biased to a distal position. When the procedure is complete, the inner shaft 188 can be moved proximally, thereby allowing the deflectable fingers 189f to move inward such that the outer sleeve 189 can be removed from the activator sleeve 186. The shaft 188 can be removed by rotating it to align the male member 188m with the female bore 184a, and pulling it proximally to pull the male member 188m through the female bore 184a.

Figure 19:
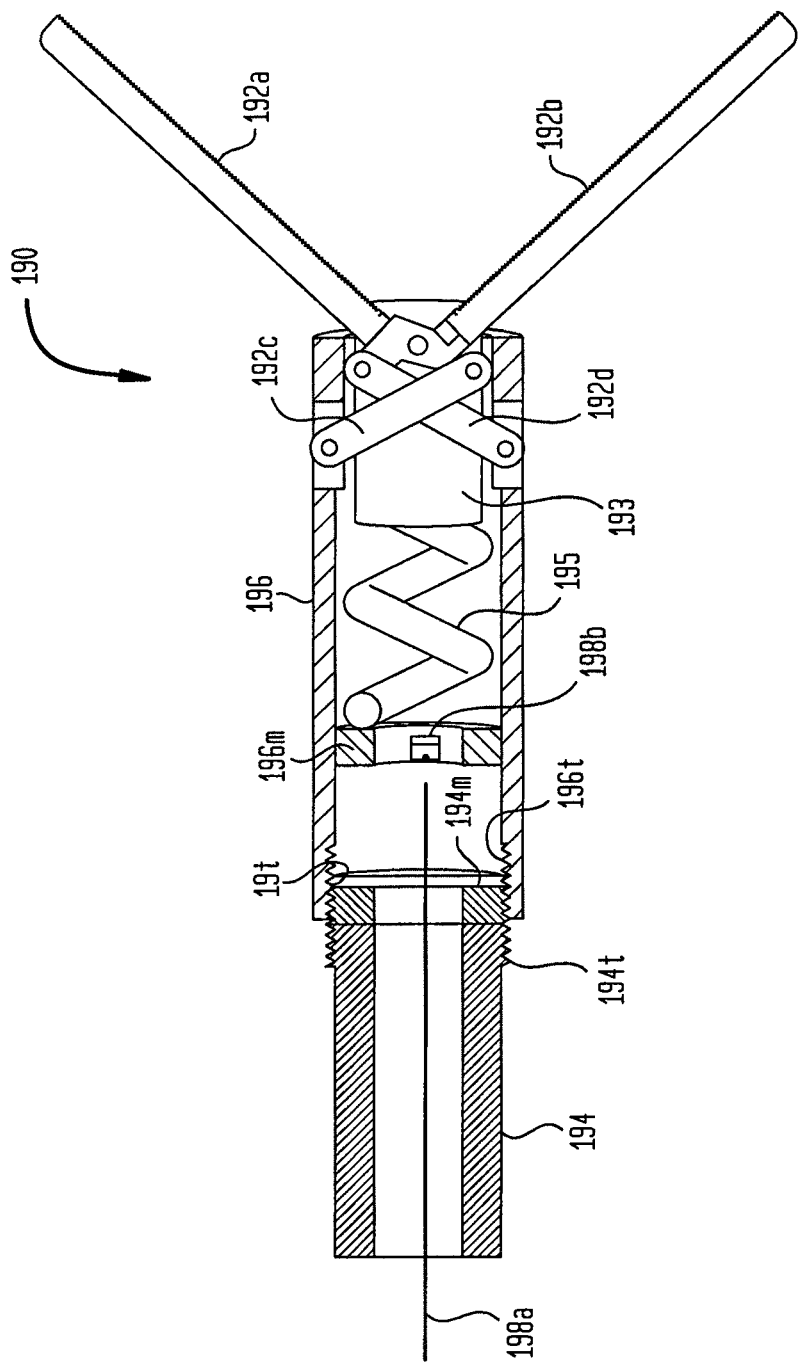
FIG. 19 is a cross-sectional view of yet another embodiment of an end effector in the form of scissors, showing a magnetic engagement mechanism.

FIG. 19 illustrates another embodiment of an end effector 190 having opposed jaws 192a, 192b. In this embodiment, the jaws 192a, 192b are in the form of graspers and the device includes a threaded engagement mechanism for attaching and detaching the end effector to and from the shaft 194, and a magnet and pusher for actuating, i.e., opening and closing, the jaws 192a, 192b, as previously described with respect to FIG. 4A. As shown, the jaws 192a, 192b are mated to a clevis 193, as described above with respect to FIGS. 18A and 18B, and connectors 192c, 192d extend between the jaws 192a, 192b and an actuating sleeve 196. The outer surface of the distal end of the shaft 194 includes threads 194t formed thereon for mating with corresponding threads 194t formed within the proximal end of the actuator sleeve 196. A magnet 194m is located on a distal end of the shaft 194 and is matable to a magnet 196m of opposite polarity disposed within a proximal end of the actuator sleeve 196. The magnets 194m, 196m can serve two purposes. First, the magnets 194m, 196m can be used to pull the shaft 194 and end effector 190 toward one another, thereby allowing the shaft 194 to be rotated and threadably mated to the end effector 190. Second, the magnets, 194m, 196m in combination with a pusher 198a, can be used to actuate the jaws 192a, 192b. In the embodiment shown in FIG. 19, the magnet 196m in the end effector 190 is slidably movable along a longitudinal axis of the device, and it is coupled to the clevis 193 by a spring 195. The magnetic force of the magnet 194m on the distal end of the shaft 194 will pull the magnet 196m within the end effector 190 proximally. The pusher 198a can thus be used to push the magnet 196m in the end effector 190 distally to cause it to apply a force to the spring 195 which in turn will move the clevis 193 distally within the actuating sleeve 196, thereby closing the jaws 192a, 192b. While the pusher 198a can abut directly against the end effector magnet 196m, in the embodiment shown in FIG. 19 the end effector magnet 196m includes an abutment or protrusion 198b formed thereon for seating the pusher. In order to release the end effector 190 from engagement with the shaft 194, the shaft 194 can be threaded in an opposite direction to disengage the shaft 194 from the end effector 190, and the pusher 198a can be used to push the magnet 196m in the end effector 190 away from and out of engagement with the magnet 194m on the shaft 194.

Figure 20:
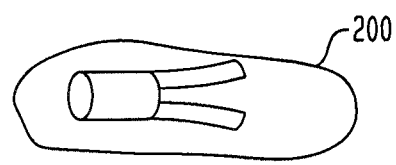
FIG. 20 is a side view of an end effector disposed within a capsule for delivery to a patient.
Figure 21A:
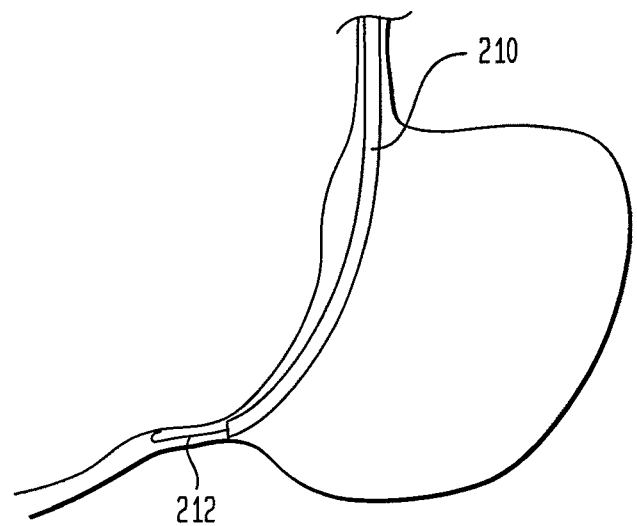
FIG. 21A is a cross-sectional view of a stomach having an endoscope inserted therethrough with a delivery wire passed through the endoscope.
Figure 21B:
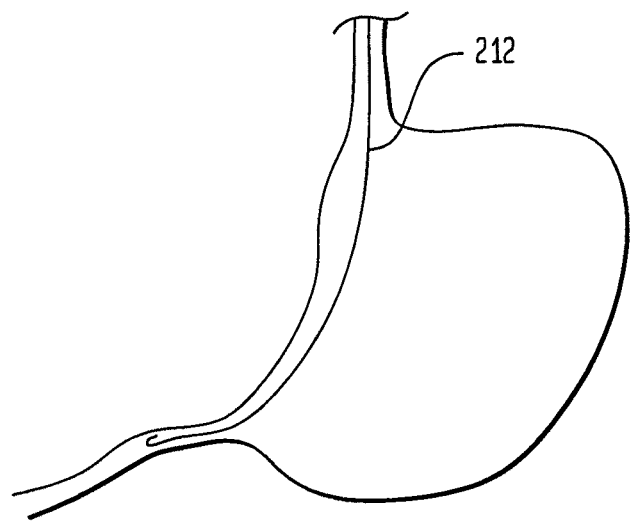
FIG. 21B is a cross-sectional view of the stomach of FIG. 21A showing the endoscope removed leaving the delivery wire in place.
Figure 21C:
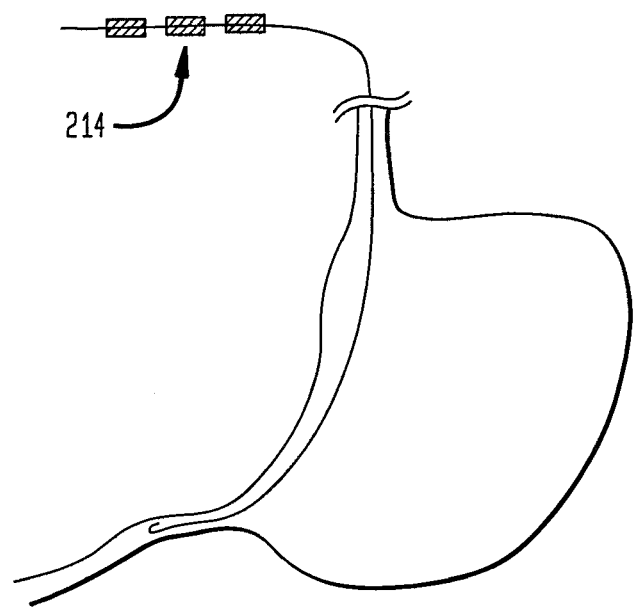
FIG. 21C is a cross-sectional view of the stomach of FIG. 21B showing several end effectors being loaded onto the delivery wire.
Figure 21D:
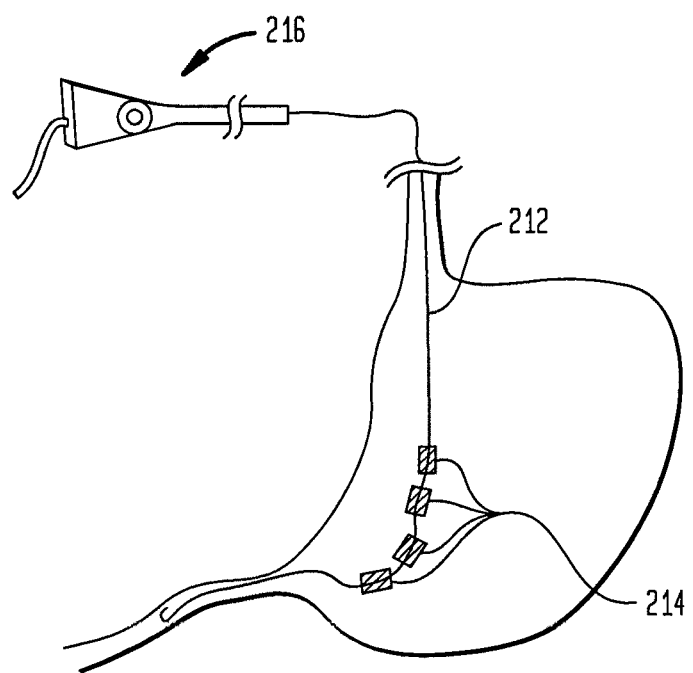
FIG. 21D is a cross-sectional view of the stomach of FIG. 21C showing an endoscope being advanced over the delivery wire.

The present invention also provides various exemplary methods for delivering the end effectors to a body cavity. In one embodiment, shown in FIG. 20, the end effector can be disposed within a dissolvable capsule 200. The capsule can be swallowed or otherwise introduced into the patient whereby the capsule will dissolve leaving the end effector in the body cavity, e.g., the stomach, for use. Alternatively, the end effectors can be delivered endoscopically. FIGS. 21A-21D illustrate one exemplary method for endoscope delivery of a plurality of end effectors. As shown, an endoscope 210 or other insertion device is first passed through a body lumen, such as through a patient's oral cavity and esophagus and into the stomach. A delivery wire 212 can be inserted through the endoscope 210, as shown in FIG. 21A, and the endoscope 210 can then be removed leaving the delivery wire 212 in place, as shown in FIG. 21B. One or more end effectors 214 can then be advanced over the delivery wire 212 and into the body cavity. A laparoscope 216 or the flexible endoscope can optionally be advanced over the delivery wire 212 to help push the end effectors 214 into the body cavity. An overtube can alternatively be used to rapidly deliver multiple end effectors to a body cavity.

Once the end effectors 214 are in the body cavity, an elongate shaft having various configurations can be inserted into the body cavity whereby it can be used to interchangeably engage each of the various end effectors to perform various surgical procedures. In one embodiment, the shaft can be delivered through the endoscope. In another embodiment, the shaft can be delivered laparoscopically, for example through an incision formed in the stomach, to interchangeably engage the various end effectors. By having all of the end effectors predisposed in the body cavity, the patient does not to be re-intubated every time a new end effector is required. Moreover, the procedure does not require a large incision to be formed in the patient. In particular, the end effectors can have a diameter that is larger than a diameter of the shaft to which they attach to. Since the end effectors are delivered endoscopically, the incision formed in the skin only needs to be large enough to receive the shaft. Moreover, the particular configuration of the various engagement mechanisms previously disclosed allows the end effectors to be attached and detached to and from the elongate shaft without the use of additional tools for holding the end effectors. Once the procedure is complete, the end effectors can be removed endoscopically, passed naturally through the body, or using various other techniques.

A person skilled in the art will appreciate that, while not shown or discussed in detail with respect to each engagement mechanism, various actuators can be used to effect movement of the various aforementioned engagement mechanisms. In general, one or more actuators can be coupled to a proximal end of a shaft, and movement of the actuator can be effective to cause various actions at the distal end of the shaft, such as attachment and detachment of an end effector to the shaft, and actuation of one or more portions of the end effector such as jaw opening and closing, clip or staple advancement, energy delivery, etc. The particular action which results from movement of an actuator will necessarily depend on the particular configuration of the device and the end effector. In an exemplary embodiment, the actuator is configured to allow a user to remotely effect an action at a distal end of the device. In particular, the distal end can be introduced into a body cavity while the proximal end extends from and remains external to the patient. The proximal end can be actuated to cause movement at the distal end of the device, thereby allowing remote activation of the distal end. This is particularly advantageous as additional tools and devices do not need to be introduced into the body cavity to assist in attaching/detaching an end effector to/from the distal end of the device, and in actuating the end effector.

Figure 22B:
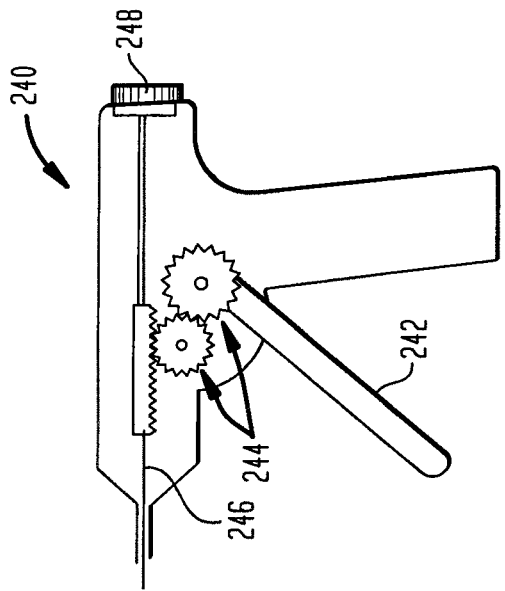
FIG. 22B is a side partially cross-sectional view of another embodiment of a handle for actuating an end effector.
Figure 22C:
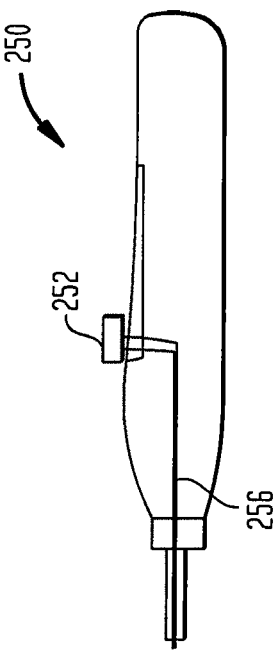
FIG. 22C is a side partially cross-sectional view of yet another embodiment of a handle for actuating an end effector.
Figure 22A:
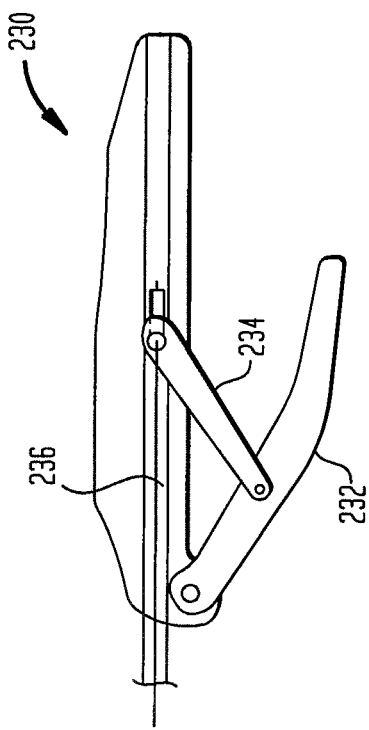
FIG. 22A is a side partially cross-sectional view of one embodiment of handle for actuating an end effector.

While virtually any actuation mechanism known in the art can be used, including levers, handles, knobs, etc., FIGS. 22A-22C illustrate certain exemplary actuators. FIG. 22A illustrates a handle 230 having a pivoting trigger 232 formed thereon. The handle 230 includes a coupling mechanism 234 extending between the trigger 232 and a proximal end of a shaft 236 to be moved. Movement of the trigger 232 toward the handle 230, i.e., into a closed position, is effective to cause the coupling mechanism 234 to move proximally thereby pulling the shaft 236 proximally. As a result, the distal end of the shaft 236 moves proximally. This can be effective, for example, to pull a clevis proximally thereby pulling opposed jaws of a grasping or cutting device together. FIG. 22B illustrates another embodiment of a handle 240 having a pivoting trigger 242 coupled thereto. In this embodiment, movement of the trigger 242 toward the handle 240, i.e., to a closed position, is effective to rotate gears 244 which cause a shaft 246 of the device to move distally. Distal movement of the shaft 246 could, for example, be effective to advance a pusher distally thereby pushing an end effector out of engagement with a distal end of the shaft. FIG. 22B also illustrates a knob 248 coupled to a proximal end of the shaft 246. Rotation of the knob 248 could, for example, be effective to rotate a distal end of the shaft 246 thereby threading the shaft 246 into a threaded bore in an end effector, or performing other actions that require axial rotation. FIG. 22C illustrates another embodiment of an actuator. In this embodiment, a handle 250 is shown having a lever 252 coupled to a proximal end of a shaft 256. The lever 252 is adapted to slid proximally and distally relative to the shaft 256, thereby moving the distal end of the shaft 256 proximally and distally. As with the handles shown in FIGS. 22A and 22B, this movement could be effective to attach/detach an end effector to/from a distal end of the shaft, and/or to actuate the end effector. A person skilled in the art will appreciate that a variety of other handles and actuators can be used to effect various movements of a shaft, including axial rotation and translation, as well as energy delivery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new and/or used instrument(s) is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A modular surgical device, comprising:
   an outer shaft having a distal end moveable between a contracted configuration and an expanded configuration;
   an end effector matable to the distal end of the outer shaft, the end effector having a bore formed at a proximal end thereof for receiving the distal end of the outer shaft; and
   an inner shaft disposed within at least a portion of the outer shaft, the inner shaft being slidable distally relative to the outer shaft to move the distal end of the outer shaft from the contracted configuration to the expanded configuration;
   wherein, in the contracted configuration the distal end of the outer shaft is configured to be removably and replaceably inserted in the bore of the end effector, and in the expanded configuration the distal end of the outer shaft is fixedly mated to the end effector and the end effector extends distally from the distal end of the outer shaft.

2. The device of claim 1, wherein the distal end of the outer shaft comprises a plurality of deflectable fingers.

3. The device of claim 2, wherein in the open configuration, flanges of the fingers engage a wall of the end effector that surrounds the bore.

4. The device of claim 2, wherein the fingers are configured to deflect radially outward when the distal end of the outer shaft moves from the closed configuration to the open configuration.

5. The device of claim 4, wherein the fingers are configured to deflect radially inward when the distal end of the outer shaft moves from the open configuration to the closed configuration.

6. The device of claim 1, wherein the distal end of the outer shaft is moveable between the open configuration and the closed configuration by advancing the inner shaft proximally relative to the outer shaft such that the inner shaft is not disposed in the distal end of the outer shaft.

7. The device of claim 1, wherein the end effector is selected from the group consisting of a needle, a snare, a needle knife, a monopolar probe, a bipolar probe, a clipping device, a retractor, a band ligator, scissors, and graspers.

8. The device of claim 1, wherein the end effector further comprises a plurality of end effectors interchangeably matable to the distal end of the outer sleeve shaft, each end effector having a bore formed at a proximal end thereof for receiving the distal end of the outer shaft.

9. A modular surgical device, comprising:
   an outer shaft having a distal end moveable between a contracted configuration and an expanded configuration;
   an end effector matable to the distal end of the outer shaft, the end effector having a bore formed at a proximal end thereof for receiving the distal end of the outer shaft; and
   an inner shaft disposed within at least a portion of the outer shaft, the inner shaft being slidable distally relative to the outer shaft to move the distal end of the outer shaft from the contracted configuration to the expanded configuration,
   wherein the inner shaft is configured to be disposed outside of the end effector immediately prior to the inner shaft moving the outer shaft to the expanded configuration, and
   wherein, in the contracted configuration the distal end of the outer shaft is configured to be removably and replaceably inserted in the bore of the end effector, and in the expanded configuration the distal end of the outer shaft is fixedly mated to the end effector.

10. The device of claim 9, wherein the distal end of the outer shaft comprises a plurality of deflectable fingers.

11. The device of claim 10, wherein in the open configuration, flanges of the fingers engage a wall of the end effector that surrounds the bore.

12. The device of claim 10, wherein the fingers are configured to deflect radially outward when the distal end of the outer shaft moves from the closed configuration to the open configuration.

13. The device of claim 9, wherein the distal end of the outer shaft is moveable between the open configuration and the closed configuration by advancing the inner shaft proximally relative to the outer shaft such that the inner shaft is not disposed in the distal end of the outer shaft.

14. The device of claim 9, wherein the end effector further comprises a plurality of end effectors interchangeably matable to the distal end of the outer sleeve shaft, each end effector having a bore formed at a proximal end thereof for receiving the distal end of the outer shaft.

15. A modular surgical device, comprising:
   an outer shaft having a distal end moveable between a contracted configuration and an expanded configuration;
   an end effector matable to the distal end of the outer shaft, the end effector having a bore formed at a proximal end thereof for receiving the distal end of the outer shaft; and
   an inner shaft disposed within at least a portion of the outer shaft, the inner shaft being slidable distally relative to the outer shaft to move the distal end of the outer shaft from the contracted configuration to the expanded configuration;
   wherein, in the contracted configuration the distal end of the outer shaft is configured to be removably and replaceably inserted in the bore of the end effector, and in the expanded configuration the distal end of the outer shaft is fixedly mated to the end effector and engages an inner wall of the bore of the end effector.

16. The device of claim 15, wherein the distal end of the outer shaft comprises a plurality of deflectable fingers.

17. The device of claim 16, wherein the fingers are configured to deflect radially outward when the distal end of the outer shaft moves from the closed configuration to the open configuration.

18. The device of claim 15, wherein the distal end of the outer shaft is moveable between the open configuration and the closed configuration by advancing the inner shaft proximally relative to the outer shaft such that the inner shaft is not disposed in the distal end of the outer shaft.

19. The device of claim 15, wherein the end effector is selected from the group consisting of a needle, a snare, a needle knife, a monopolar probe, a bipolar probe, a clipping device, a retractor, a band ligator, scissors, and graspers.

20. The device of claim 15, wherein the end effector further comprises a plurality of end effectors interchangeably matable to the distal end of the outer sleeve shaft, each end effector having a bore formed at a proximal end thereof for receiving the distal end of the outer shaft.

* * * * *